(12) United States Patent
Razzaque et al.

(10) Patent No.: US 10,188,467 B2
(45) Date of Patent: Jan. 29, 2019

(54) SURGICAL GUIDANCE INTERSECTION DISPLAY

(71) Applicant: InnerOptic Technology, Inc., Hillsborough, NC (US)

(72) Inventors: Sharif Razzaque, Chapel Hill, NC (US); Andrei State, Chapel Hill, NC (US); Luv Kohli, Durham, NC (US); Brian Heaney, Durham, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 0 days.

(21) Appl. No.: 14/968,445

(22) Filed: Dec. 14, 2015

(65) Prior Publication Data

US 2016/0166336 A1 Jun. 16, 2016

Related U.S. Application Data

(60) Provisional application No. 62/091,238, filed on Dec. 12, 2014.

(51) Int. Cl.
*A61B 1/00* (2006.01)
*A61B 5/027* (2006.01)
(Continued)

(52) U.S. Cl.
CPC .............. *A61B 34/20* (2016.02); *A61B 34/25* (2016.02); *A61B 90/37* (2016.02); *A61B 2034/2048* (2016.02); *A61B 2034/2051* (2016.02); *A61B 2034/2055* (2016.02); *A61B 2034/2059* (2016.02); *A61B 2034/2072* (2016.02);
(Continued)

(58) Field of Classification Search
None
See application file for complete search history.

(56) References Cited

U.S. PATENT DOCUMENTS 3,556,079 A 1/1971 Omizo
4,058,114 A 11/1977 Soldner
(Continued)

FOREIGN PATENT DOCUMENTS

AU 7656896 A 5/1997
AU 9453898 A 4/1999
(Continued)

OTHER PUBLICATIONS

U.S. Appl. No. 11/828,826 including its ongoing prosecution history, including without limitation Office Actions, Amendments, Remarks, and any other potentially relevant documents, filed Jul. 26, 2007, Keller et al.
(Continued)

*Primary Examiner* — Soo Shin
(74) *Attorney, Agent, or Firm* — Knobbe, Martens, Olson & Bear, LLP

(57) ABSTRACT

A system and method for providing image guidance for placement of one or more medical devices at a target location. The system can determine one or more intersections between a medical device and an image region based at least in part on first emplacement data and second emplacement data. Using the determined intersections, the system can cause one or more displays to display perspective views of image guidance cues, including an intersection indicator in a virtual 3D space.

20 Claims, 13 Drawing Sheets

(51) Int. Cl.
*A61B 34/20* (2016.01)
*A61B 90/00* (2016.01)
*A61B 34/00* (2016.01)
*A61B 90/50* (2016.01)

(52) U.S. Cl.
CPC ... *A61B 2090/364* (2016.02); *A61B 2090/372* (2016.02); *A61B 2090/378* (2016.02); *A61B 2090/3925* (2016.02); *A61B 2090/3937* (2016.02); *A61B 2090/502* (2016.02)

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,158,088 A | 10/1992 | Nelson et al. |
| 5,161,536 A | 11/1992 | Vikomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,967,991 A | 10/1999 | Gardineer et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olsdat |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |

(56) References Cited

U.S. PATENT DOCUMENTS

| | | |
|---|---|---|
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Steinar et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Oltad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 | 9/2009 | Accomazzi et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 | 6/2010 | Dean et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 9,107,698 B2 | 8/2015 | Razzaque et al. |
| 9,282,947 B2 | 3/2016 | Razzaque et al. |
| 9,364,294 B2 | 6/2016 | Razzaque et al. |
| 9,398,936 B2 | 7/2016 | Razzaque et al. |
| 9,659,345 B2 | 5/2017 | Razzaque et al. |
| 9,675,319 B1 | 6/2017 | Razzaque et al. |
| 9,901,406 B2 | 2/2018 | State et al. |
| 9,949,700 B2 | 4/2018 | Razzaque et al. |
| 2001/0007919 A1 | 7/2001 | Shahidi |
| 2001/0016804 A1 | 8/2001 | Cunningham et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzie, III |
| 2002/0077543 A1 | 6/2002 | Grzeszczuk et al. |
| 2002/0103431 A1 | 8/2002 | Toker et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |

(56) References Cited

U.S. PATENT DOCUMENTS

| | | |
|---|---|---|
| 2004/0249282 A1 | 12/2004 | Olstad |
| 2004/0254454 A1 | 12/2004 | Kockro |
| 2005/0010098 A1 | 1/2005 | Frigstad et al. |
| 2005/0085717 A1 | 4/2005 | Shahidi |
| 2005/0085718 A1 | 4/2005 | Shahidi |
| 2005/0090742 A1 | 4/2005 | Mine et al. |
| 2005/0107679 A1 | 5/2005 | Geiger et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0251148 A1 | 11/2005 | Friedrich |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0122495 A1 | 6/2006 | Kienzle |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kjell et al. |
| 2007/0270718 A1 | 11/2007 | Rochetin et al. |
| 2007/0276234 A1 | 11/2007 | Kristofferson |
| 2007/0291000 A1 | 12/2007 | Liang et al. |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0146939 A1 | 6/2008 | McMorrow et al. |
| 2008/0161824 A1 | 7/2008 | McMillen |
| 2008/0183080 A1 | 7/2008 | Abraham |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0036902 A1 | 2/2009 | DeMaio et al. |
| 2009/0105597 A1 | 4/2009 | Abraham |
| 2009/0118613 A1 | 5/2009 | Krugman et al. |
| 2009/0118724 A1 | 5/2009 | Zvuloni et al. |
| 2009/0131783 A1 | 5/2009 | Jenkins et al. |
| 2009/0137907 A1 | 5/2009 | Takimoto et al. |
| 2009/0196480 A1 | 8/2009 | Nields et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0152570 A1 | 6/2010 | Navab |
| 2010/0185087 A1 | 7/2010 | Nields et al. |
| 2010/0198045 A1 | 8/2010 | Razzaque et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0296718 A1 | 11/2010 | Ostrovsky-Berman et al. |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Clements et al. |
| 2011/0043612 A1 | 2/2011 | Keller et al. |
| 2011/0046483 A1 | 2/2011 | Fuchs et al. |
| 2011/0046486 A1 | 2/2011 | Shin et al. |
| 2011/0057930 A1 | 3/2011 | Keller |
| 2011/0082351 A1 | 4/2011 | Razzaque et al. |
| 2011/0130641 A1 | 6/2011 | Razzaque et al. |
| 2011/0137156 A1* | 6/2011 | Razzaque ............... A61B 34/20 600/424 |
| 2011/0201915 A1 | 8/2011 | Gogin et al. |
| 2011/0201976 A1 | 8/2011 | Sanghvi et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0101370 A1 | 4/2012 | Razzaque et al. |
| 2012/0108955 A1 | 5/2012 | Razzaque et al. |
| 2012/0138658 A1 | 6/2012 | Ullrich et al. |
| 2012/0143029 A1 | 6/2012 | Silverstein et al. |
| 2012/0143055 A1 | 6/2012 | Cheng et al. |
| 2012/0165679 A1 | 6/2012 | Orome et al. |
| 2012/0237105 A1* | 9/2012 | Mielekamp ............ G06T 19/00 382/132 |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0096497 A1 | 4/2013 | Duindam et al. |
| 2013/0132374 A1 | 5/2013 | Olstad et al. |
| 2013/0151533 A1 | 6/2013 | Udupa et al. |
| 2013/0178745 A1 | 7/2013 | Kyle et al. |
| 2013/0197357 A1* | 8/2013 | Green ................. A61B 8/0841 600/424 |
| 2013/0218024 A1 | 8/2013 | Boctor et al. |
| 2013/0249787 A1 | 9/2013 | Morimoto |
| 2014/0016848 A1 | 1/2014 | Razzaque et al. |
| 2014/0051987 A1 | 2/2014 | Kowshik et al. |
| 2014/0078138 A1 | 3/2014 | Martin et al. |
| 2014/0180074 A1 | 6/2014 | Green |
| 2014/0201669 A1 | 7/2014 | Liu et al. |
| 2014/0275760 A1 | 9/2014 | Lee et al. |
| 2014/0275810 A1 | 9/2014 | Keller et al. |
| 2014/0275997 A1 | 9/2014 | Chopra et al. |
| 2014/0343404 A1 | 11/2014 | Razzaque et al. |
| 2014/0350390 A1 | 11/2014 | Kudavelly et al. |
| 2016/0117857 A1* | 4/2016 | State ..................... A61B 34/20 345/420 |
| 2016/0166334 A1 | 6/2016 | Razzaque et al. |
| 2016/0196694 A1 | 7/2016 | Lindeman |
| 2016/0270862 A1 | 9/2016 | Fuchs et al. |
| 2017/0024903 A1 | 1/2017 | Razzaque |
| 2017/0065352 A1 | 3/2017 | Razzaque et al. |
| 2017/0128139 A1 | 5/2017 | Razzaque et al. |

(56) References Cited

U.S. PATENT DOCUMENTS

| | | | |
|---|---|---|---|
| 2017/0323424 | A1 | 11/2017 | Razzaque et al. |
| 2017/0348067 | A1 | 12/2017 | Krimsky |
| 2017/0360395 | A1 | 12/2017 | Razzaque et al. |
| 2018/0116731 | A1 | 5/2018 | State et al. |
| 2018/0263713 | A1 | 9/2018 | State |
| 2018/0289344 | A1 | 10/2018 | Green et al. |

FOREIGN PATENT DOCUMENTS

| | | |
|---|---|---|
| AU | 1719601 A | 6/2001 |
| AU | 9036301 A | 3/2002 |
| AU | 2003297225 A1 | 7/2004 |
| AU | 2001290363 B2 | 2/2006 |
| BR | 0113882 A | 7/2003 |
| CA | 2420382 C | 4/2011 |
| DE | 60126798 T2 | 10/2007 |
| EP | 0 427 358 | 5/1991 |
| EP | 1955284 | 8/2008 |
| JP | S63-290550 A | 11/1988 |
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/005768 | 2/1996 |
| WO | WO 97/015249 | 5/1997 |
| WO | WO 97/017014 | 5/1997 |
| WO | WO1997029682 | 8/1997 |
| WO | WO 99/26534 | 6/1999 |
| WO | WO 01/039683 | 6/2001 |
| WO | WO 03/032837 | 4/2003 |
| WO | WO 03/034705 | 4/2003 |
| WO | WO 03/105289 | 12/2003 |
| WO | WO 05/010711 | 2/2005 |
| WO | WO 07/019216 | 2/2007 |
| WO | WO 07/067323 A2 | 6/2007 |
| WO | WO 07/067323 A3 | 9/2007 |
| WO | WO 08/017051 A2 | 2/2008 |
| WO | WO 09/063423 | 5/2009 |
| WO | WO 09/094646 | 7/2009 |
| WO | WO 10/057315 | 5/2010 |
| WO | WO 10/096419 A2 | 8/2010 |
| WO | WO 11/014687 A2 | 2/2011 |
| WO | WO 12/169990 | 12/2012 |
| WO | WO 13/116240 | 8/2013 |
| WO | WO 18/080844 | 5/2018 |

OTHER PUBLICATIONS

"3D Laparoscope Technology," http://www.inneroptic.com/tech_3DL.htm, copyright 2007 InnerOptic Technology, Inc. printed Sep. 19, 2007, 2 pages.

"Cancer Facts & Figures 2004," www.cancer.org/downloads/STT/CAFF_finalPWSecured.pdf, copyright 2004 American Cancer Society, Inc., printed Sep. 19, 2007, 60 pages.

"David Laserscanner <-Latest News <-Institute for Robotics and Process Control <-Te . . . ," http://www/rob.cs.tu-bs.de/en/news/david, printed Sep. 19, 2007, 1 page.

"Laser scanned 3d model Final" video, still image of video attached, http://www.youtube.com/watch?v+DaLgIgmoUf8, copyright 2007 YouTube, LLC, printed Sep. 19, 2007, 2 pages.

"Olympus Endoscopic Ultrasound System," www.olympusamerica.com/msg_section/download_brochures/135_b_3gfum130.pdf, printed Sep. 20, 2007, 20 pages.

"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.

"Robbins, Mike—Computer Vision Research—Stereo Depth Perception," http://www.compumike.com/vision/stereodepth.php, copyright 2007 Michael F. Robbins, printed Sep. 19, 2007, 3 pages.

"RUE, Registered Ultrasound-Endoscope," copyright 2007 InnerOptic Technology, Inc., 2 pages.

Advertisement, "Inspeck 3DC 3D Capturor," Inspeck 3DC 3D Capturor (www.inspeck.com), 1998.

Advertisement, "Virtual 3D High Speed Non-Contact Surface Perception," Virtual 3-D Technologies Corporation (www.virtual3dtech.com)., Dec. 21, 1998.

Advertisements, "Virtuoso," Visual Interface, Inc. (www.visint.com), Dec. 21, 1998.

Akka, "Automatic Software Control of Display Parameters for Stereoscopic Graphics Images," SPIE vol. 1669: Stereoscopic Displays and Applications III, pp. 31-38 (1992).

Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.

Aylward et al., Analysis of the Parameter Space of a Metric for Registering 3D Vascular Images, in W. Niessen and M. Viergever (Eds.): MICCAI 2001, LNCS 2208, pp. 932-939, 2001.

Aylward et al., Registration and Analysis of Vascular Images, International Journal of Computer Vision 55(⅔), 123-138, 2003.

Aylward, et al., Intra-Operative 3D Ultrasound Augmentation, Proceedings of the IEEE International Symposium on Biomedical Imaging, Washington, Jul. 2002.

Azuma et al., "Improving Static and Dynamic Registration in an Optical See-Through HMD," Paper Presented at SIGGRAPH '94 Annual Conference in Orlando, FL, 17 pages (1994).

Azuma, "A Survey of Augmented Reality," Presence: Teleoperators and Virtual Environments 6, 4:1-48 (Aug. 1997).

Badler et al., "Simulating Humans: Computer Graphics, Animation, and Control," Oxford University Press (1993).

Bajura, Michael et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.

Benavides et al., "Multispectral digital colposcopy for in vivo detection of cervical cancer," Optics Express; May 19, 2003; 11(10) Optical Society of America; USA.

Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.

Billinghurst, M. et al., Research Directions in Handheld AR; Int. J. of Virtual Reality 5(2),51-58 (2006).

Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.

Bouguet, Jean-Yves, "Camera Calibration Toolbox for Matlab," www.vision.caltech.edu/bouguetj/calib_doc, printed Sep. 20, 2007, 5 pages.

Buxton et al.; "Colposcopically directed punch biopsy: a potentially misleading investigation," British Journal of Obstetrics and Gynecology; Dec. 1991; 98:1273-1276.

Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.

Cancer Prevention & Early Detection Facts & Figures 2004; National Center for Tobacco-Free Kids; 2004; American Cancer Society; USA.

Cantor et al., "Cost-Effectiveness Analysis of Diagnosis and Management of Cervical Squamous Intraepithelial Lesions," Diagnostic Strategies for SILs; Feb. 1998; 91(2):270-277.

Catalano et al. "Multiphase helical CT findings after percutaneous ablation procedures for hepatocellular carcinoma." Abdom. Imaging, 25(6),2000, pp. 607-614.

(56) References Cited

OTHER PUBLICATIONS

Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.

Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.

Deering, Michael "High Resolution Virtual Reality." Proceedings of SIGGRAPH '92, Computer Graphics, 26(2), 1992, pp. 195-202.

Depiero et al., "3-D Computer Vision Using Structured Light: Design, Calibration and Implementation Issues," The University of Tennessee, pp. 1-46, (1996).

Dodd, G.D. et al. "Minimally invasive treatment of malignant hepatic tumors: at the threshold of a major breakthrough." Radiographies 20(1),2000, pp. 9-27.

Drascic et al., "Perceptual Issues in Augmented Reality," SPIE vol. 2653: Stereoscopic Displays and Virtual Reality Systems III, pp. 123-134 (Feb. 1996).

Dumoulin, C.L. et al, Real-Time Position Monitoring of Invasive Devices Using Magnetic Resonance, Magnetic Resonance in Medicine, vol. 29, Issue 3, Mar. 1993, pp. 411-415.

Fahey et al., "Meta-analysis of Pap Test Accuracy; American Journal of Epidemiology," 1995 141(7):680-689; The John Hopkins University School of Hygiene and Public Health; USA.

Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).

Fronheiser et al., Real-Time 3D Color Doppler for Guidance of Vibrating Interventional Devices, IEEE Ultrasonics Symposium, pp. 149-152 (2004).

Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications/AugRealVis_LaparoSurg98.pdf, printed Sep. 20, 2007, 10 pages.

Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.

Fuchs, et al.: "Virtual Environments Technology to Aid Needle Biopsies of the Breast," Health Care in the Information Age, Ch. 6, pp. 60-61, Presented in San Diego, Jan. 17-20, 1996, published by IOS Press and Ohmsha Feb. 1996.

Fuhrmann A. et al., Comprehensive calibration and registration procedures for augmented reality; Proc. Eurographics Workshop on Virtual Environments 2001,219--228 (2001).

Garrett, William F. et al., "Real-Time Incremental Visualization of Dynamic Ultrasound Volumes Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Georgakoudi et al., "Trimodal spectroscopy for the detection and characterization of cervical precancers in vivo," American Journal of Obstetrics and Gynecology; Mar. 2002; 186(3):374-382; USA.

StereoMirror Technology Webpage, http://www.planar.com/products/flatpanel_monitors/stereoscopic/ (Printed Dec. 29, 2011).

Herline et al., Surface Registration for Use in Interactive, Image-Guided Liver Surgery, Computer Aided Surgery 5:11-17 (2000).

Holloway, R.; Registration Error Analysis for Augmented Reality; Presence: Teleoperators and Virtual Environments 6(4), 413--432 (1997).

Hornung et al., "Quantitative near-infrared spectroscopy of cervical dysplasia in vivo," Human Reproduction; 1999; 14(11):2908-2916; European Society of Human Reproduction and Embryology.

Howard, M.D., et al.: "An Electronic Device for Needle Placement during Sonographically Guided Percutaneous Intervention", Radiology 2001; 218:905-911.

InnerAim Brochure; 3D Visualization Software for Simpler, Safer, more Precise Aiming, Published no earlier than Apr. 1, 2010.

InVision System Brochure; A "GPS" for Real-Time 3D Needle Visualization & Guidance, Published no earlier than Mar. 1, 2008.

InVision User Manual; Professional Instructions for Use, Published no earlier than Dec. 1, 2008.

Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.

Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.

Kadi, A Majeed, et al., Design and Simulation of an Articulated Surgical Arm for Guiding Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.

Kanbara et al., "A Stereoscopic Video See-through Augmented Reality System Based on Real-time Vision-Based Registration," Nara Institute of Science and Technology, pp. 1-8 (2000).

Kato, Amami, et al., A frameless, armless navigational system for computer-assisted neurosurgery, Journal of Neurosurgery, vol. 74, No. 5, May 1991, pp. 845-849.

Keller et al., "What is it in Head Mounted Displays (MDs) that really make them all so terrible?," pp. 1-8 (1998).

Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.

Lee, et al., "Modeling Real Objects Using Video See-Through Augmented Reality," Proceedings of the Second International Symposium on Mixed Reality, ISMR 2001, pp. 19-26 (Mar. 14-15, 2001).

Lee et al., "Modeling Real Objects Using Video See-Through Augmented Reality," Presence, 11(2):144-157 (Apr. 2002).

Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.

Levy, et al., An Internet-Connected, Patient Specific, Deformable Brain Atlas Integrated into a Surgical Navigation System, Journal of Digital Imaging, vol. 10, No. 3. Suppl. 1 Aug. 1997: pp. 231-237.

Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.

Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).

Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.

Milgram et al., "Adaptation Effects in Stereo due to Online Changes in Camera Configuration," SPIE vol. 1669-13, Stereoscopic Displays and Applications III, 17 pages (1992).

Mitchell et al., "Colposcopy for the Diagnosis of Squamous Intraepithelial lesions: A metaanalysis," Obstetrics and Gynecology; Apr. 1998; 91(4):626-631.

Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.

Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.

(56) References Cited

OTHER PUBLICATIONS

Ohbuchi et al. "An Incremental Volume Rendering Algorithm for Interactive 3D Ultrasound Imaging", UNC-CH Computer Science Technical Report TR91-003, (1991).

Ohbuchi et al., "Incremental Volume Reconstruction and Rendering for 3D Ultrasound Imaging," Visualization in Biomedical Computing, SPIE Proceedings, pp. 312-323, (Oct. 13, 1992).

Ohbuchi, "Incremental Acquisition and Visualization of 3D Ultrasound Images," Ph.D. Dissertation, UNC-CH Computer Science Technical Report TR95--023, (1993).

Progue, Brian W. et al., "Analysis of acetic acid-induced whitening of high-grade squamous intraepitheliallesions," Journal of Biomedical Optics; Oct. 2001; 6(4):397-403.

Raij, A.B., et al., Comparing Interpersonal Interactions with a Virtual Human to Those with a Real Human; IEEE Transactions on Visualization and Computer Graphics 13(3), 443-457 (2007).

Raz et al, Real-Time Magnetic Resonance Imaging—Guided Focal Laser Therapy in Patients with Low-Risk Prostate Cancer, European Urology 58, pp. 173-177. Mar. 12, 2010.

Robinett et al., "A Computational Model for the Stereoscopic Optics of a Head-Mounted Display," SPIE vol. 1457, Stereoscopic Displays and Applications II, pp. 140-160 (1991).

Rolland et al., Towards Quantifying Depth and Size Perception in Virtual Environments, Presence: Teleoperators and Virtual Environments, Winter 1995, vol. 4, Issue 1, pp. 1-21 and 24-49.

Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.

Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.

Screenshots from video produced by the University of North Carolina, produced circa 1992.

State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.

State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.

State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.

State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).

State et al., "Superior Augmented Reality Registration by Integrating Landmark Tracking and Magnetic Tracking," ACM SIGGRAPH Computer Graphics, Proceedings of SIGGRAPH 1996, 10 pages (Aug. 1996).

State et al., "Technologies for Augmented Reality Systems: Realizing Ultrasound-Guided Needle Biopsies," Proc. SIGGRAPH 96 (New Orleans, LA, Aug. 4-9, 1996). In Computer Graphics Proceedings, Annual Conference Series, 1996, ACM SIGGRAPH, pp. 439-446.

State, Andrei "Exact Eye Contact with Virtual Humans." Proc. IEEE International Workshop on Human Computer Interaction 2007 (Rio de Janeiro, Brazil, Oct. 20, 2007), pp. 138-145.

State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.

Symons et al., "What are You Looking at? Acuity for Triadic Eye Gaze," J. Gen. Psychology 131(4), pp. 451-469 (2004).

Takacs et al., "The Virtual Human Interface: A Photorealistic Digital Human," IEEE Computer Graphics and Applications 23(5), pp. 38-45 (2003).

Takagi et al., "Development of a Stereo Video See-through HMD for AR Systems," IEEE, pp. 68-77 (2000).

Takayama et al., "Virtual Human with Regard to Physical Contact and Eye Contact," Entertaining Computing 2005, LNCS, vol. 3711, pp. 268-278 (2005).

Ultraguide 1000 System, Ultraguide, www.ultraguideinc.com, 1998.

Van Staveren et al., "Light Scattering in Intralipid-10% in the wavelength range of 400-1100 nm," Applied Optics; Nov. 1991; 30(31):4507-4514.

Viola et al., "Alignment by Maximization of Mutual Information," International Journal of Computer Vision, vol. 24, No. 2, pp. 1-29 (1997).

Viola, Paul A., Alignment by Maximization of Mutual Information, Ph.D. Dissertation, MIT-Artificial Intelligence Laboratory Technical Report No. 1548 (Jun. 1995).

Ware et al., "Dynamic Adjustment of Stereo Display Parameters," IEEE Transactions on Systems, Many and Cybernetics, 28(1):1-19 (1998).

Watson et al., "Using Texture Maps to Correct for Optical Distortion in Head-Mounted Displays," Proceedings of the Virtual Reality Annual Symposium '95, IEEE, pp. 1-7 (1995).

Welch, Hybrid Self-Tracker: An Inertial/Optical Hybrid Three-Dimensional Tracking System, University of North Carolina Chapel Hill Department of Computer Science, TR 95-048 (1995).

Yinghui et al., Real-Time Deformation Using Modal Analysis on Graphics Hardware, Graphite 2006, Kuala Lumpur, Malaysia, Nov. 29-Dec. 2, 2006.

Zitnick et al., "Multi-Base Stereo Using Surface Extraction," Visual Interface Inc., (Nov. 24, 1996).

U.S. Appl. No. 15/041,868 including its ongoing prosecution history, including without limitation Office Actions, Amendments, Remarks, and any other potentially relevant documents, filed Feb. 11, 2016, Fuchs et al.

U.S. Appl. No. 15/068,323 including its ongoing prosecution history, including without limitation Office Actions, Amendments, Remarks, and any other potentially relevant documents, filed Mar. 11, 2016, Razzaque et al.

U.S. Appl. No. 15/415,398 including its ongoing prosecution history, including without limitation Office Actions, Amendments, Remarks, and any other potentially relevant documents, filed Jan. 25, 2017, State et al.

U.S. Appl. No. 15/598,616 including its ongoing prosecution history, including without limitation Office Actions, Amendments, Remarks, and any other potentially relevant documents, filed May 18, 2017, Razzaque et al.

"Sony Introduces Head-Mounted Display for Endoscopic Surgery" (Jul. 23, 2013), retrieved Sep. 27, 2016, 5 pages, available at http://www.medgaget.com/2013/07/sony-introduces-head-mounted-display-for-endoscopic-surgery.html.

"Sony Introduces 'head-mount image processing unit' for endoscopic image display" (Jul. 23, 2013), retrieved Sep. 27, 2016, 8 pages, available at http://www.sony.net/SonyInfo/News/Press/201307/13-085E/index.html.

U.S. Appl. No. 15/799,639 including its ongoing history, including without limiation Office Actions, Amendments, Remarks, and any other potentially relevant documents, dated Oct. 31, 2017, Green et al.

Obround Agreements and Conferences Overview, various dates, 3 pages.

U.S. Appl. No. 15/882,709, filed Jan. 29, 2018, State et al.

U.S. Appl. No. 15/995,059, filed Apr. 17, 2018, Kohli et al.

Press Release: Pathfinder and InnerOptic Announce Technology Integration to Enhance Visualization and Outcomes in Liver Surgery, Published Mar. 6, 2013.

(56) References Cited

OTHER PUBLICATIONS

"InnerOptic's AIM System Receives DA 501(K) Clearance", InnerOptic Technology, Inc., Sep. 18, 2012.
Ohnesorge, Lauren K., "InnerOptic technology wins FDA approval", Triangle Business Journal, Sep. 19, 2012.
"AIM 3D Needle Placement Software from InnerOptic", Medgadget, Sep. 21, 2012.
U.S. Appl. No. 16/052,289 including its ongoing prosecution history, including without limitation Office Actions, Amendments, Remarks, and any other potentially relevant documents, dated Aug. 1, 2018, Kohli et al.
AIM Section 5: 510k Summary, submitted by InnerOptic Technology, Inc., in 5 pages, submission date May 17, 2012.
Lindeman, A Low-Cost, Low-latency Approach to Dynamic Immersion in Occlusive Head-Mounted Displays, University of Canterbury, WPI,- Poster from IEEE VR 2016, Mar. 19-23, 2016.

* cited by examiner

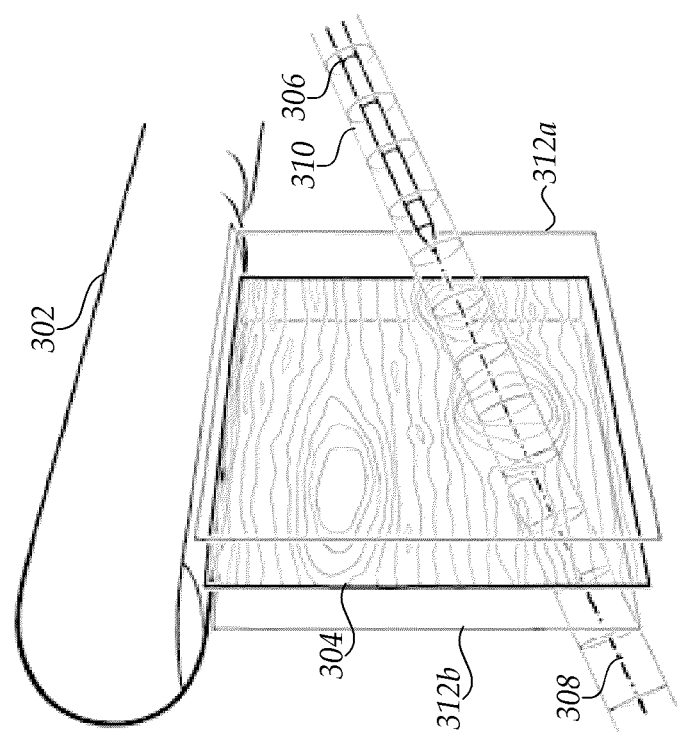
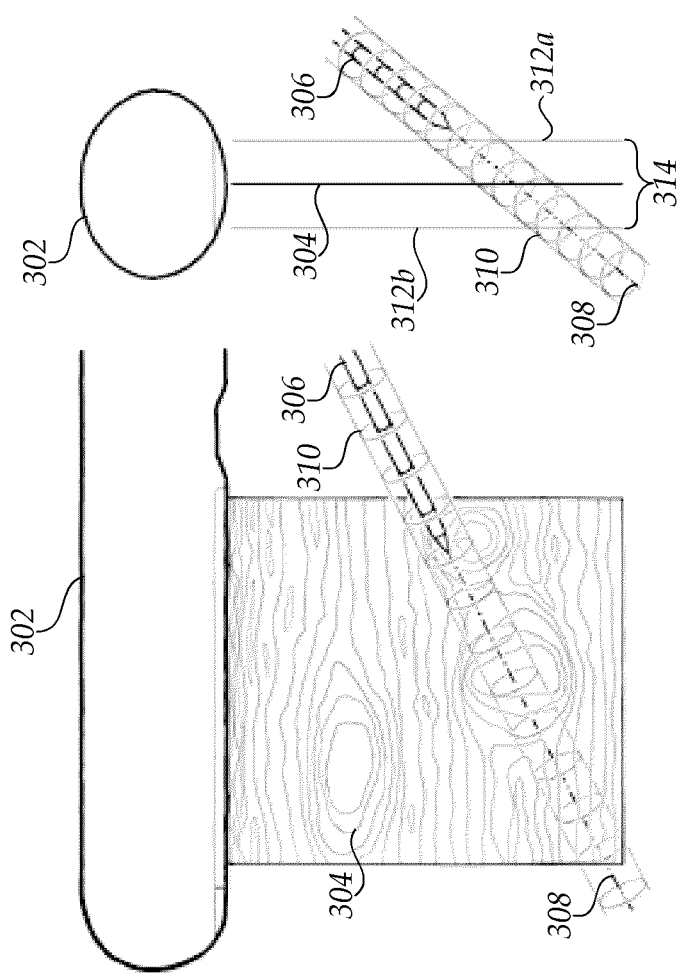

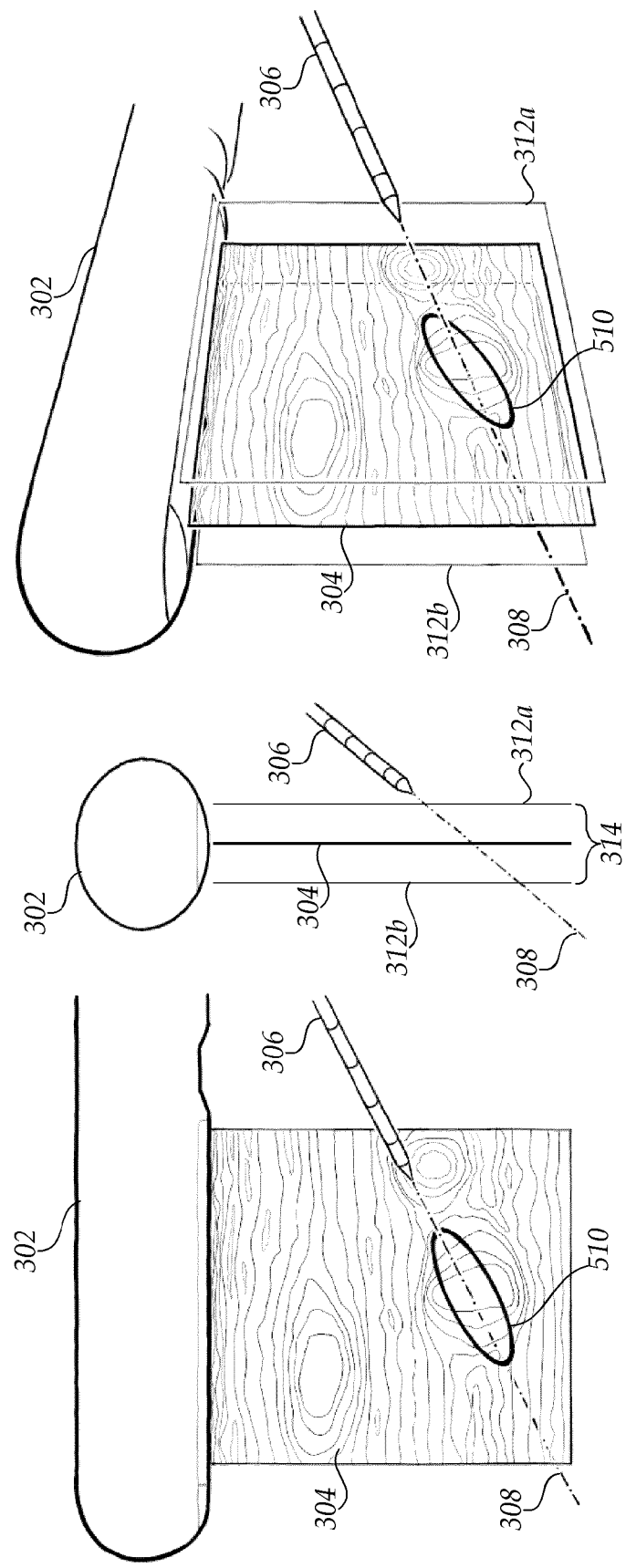

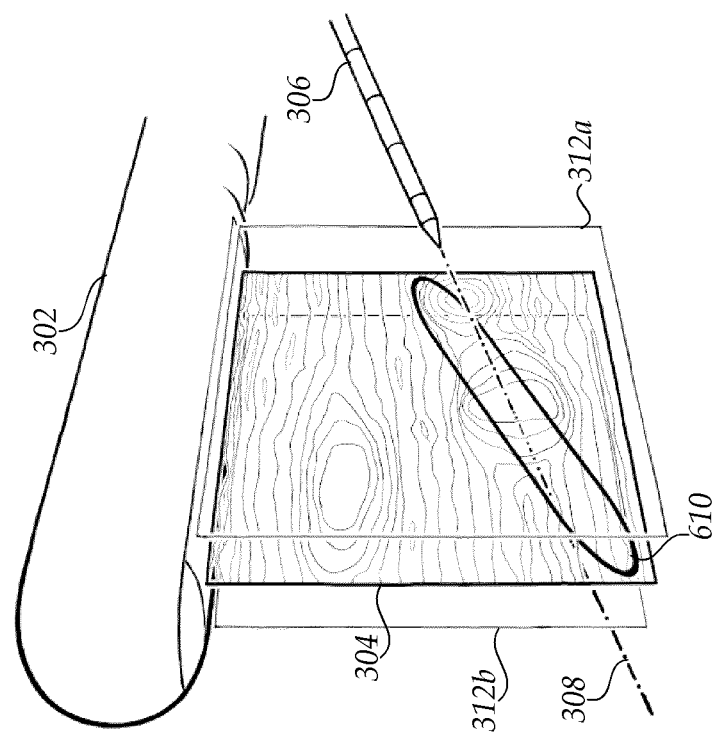
FIG. 6C
FIG. 6B
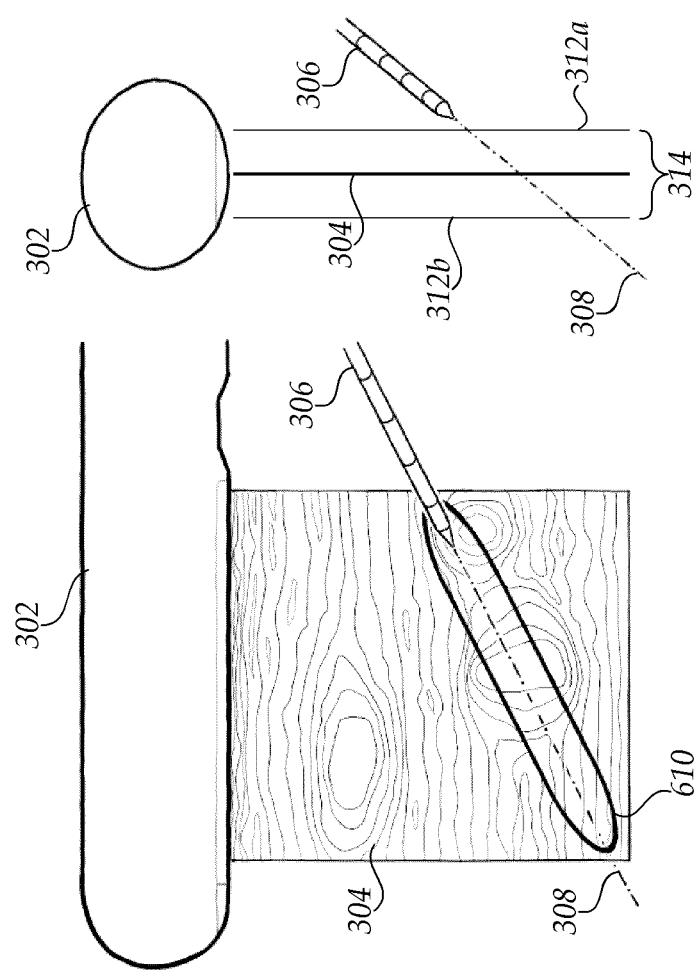
FIG. 6A

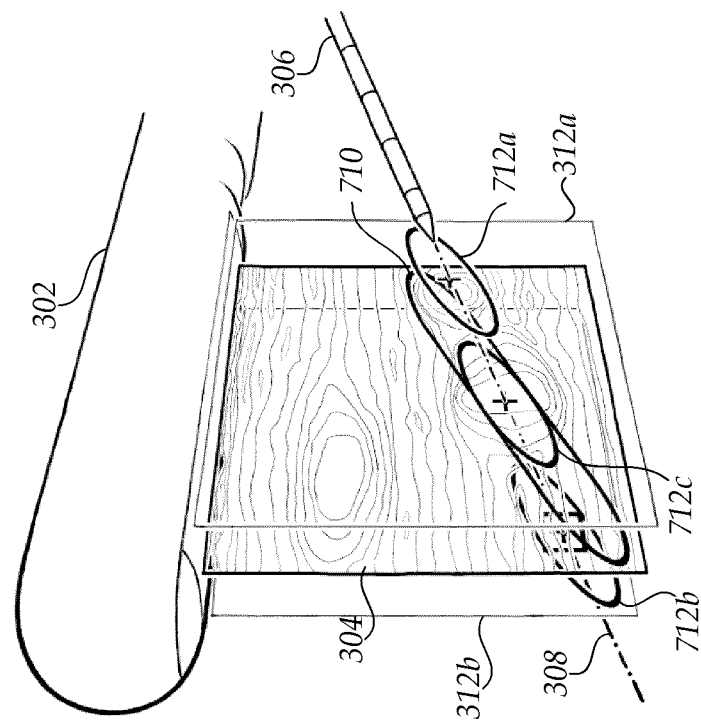
FIG. 7C
FIG. 7B
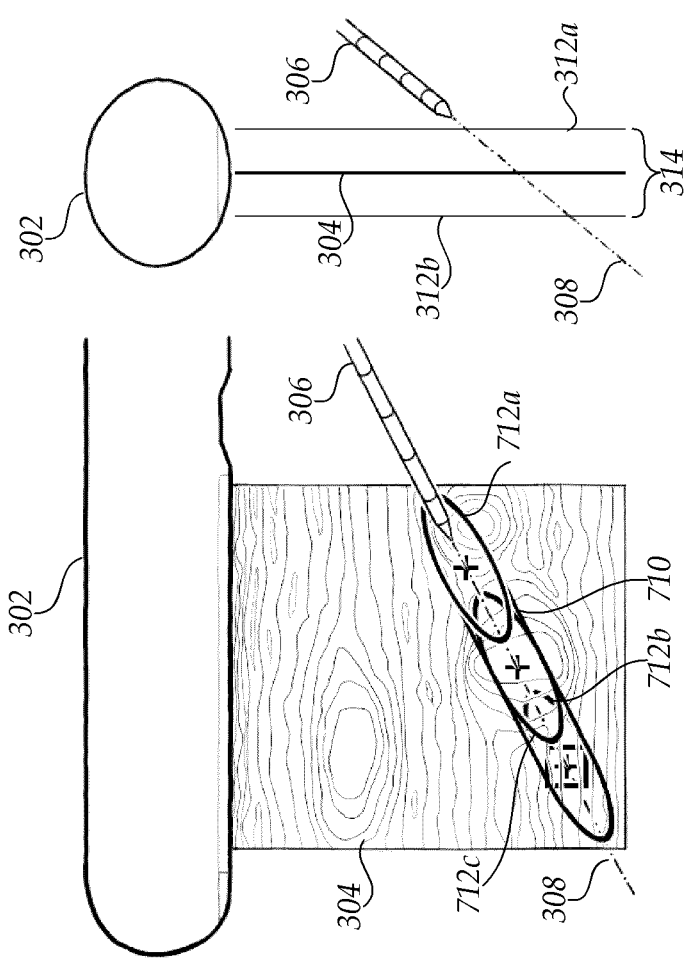
FIG. 7A

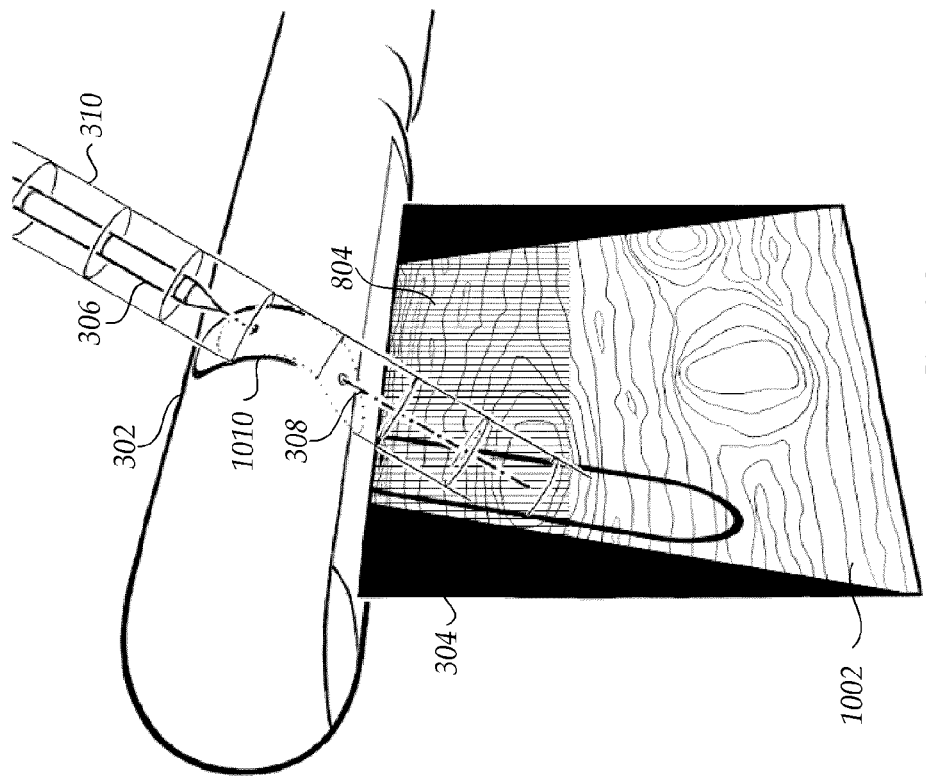
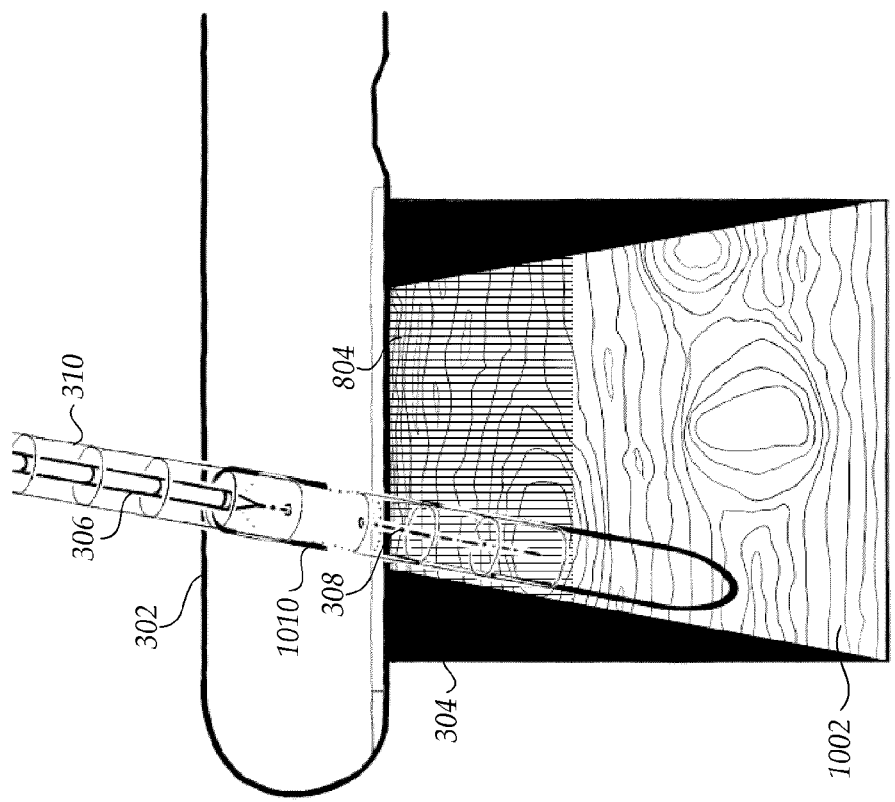

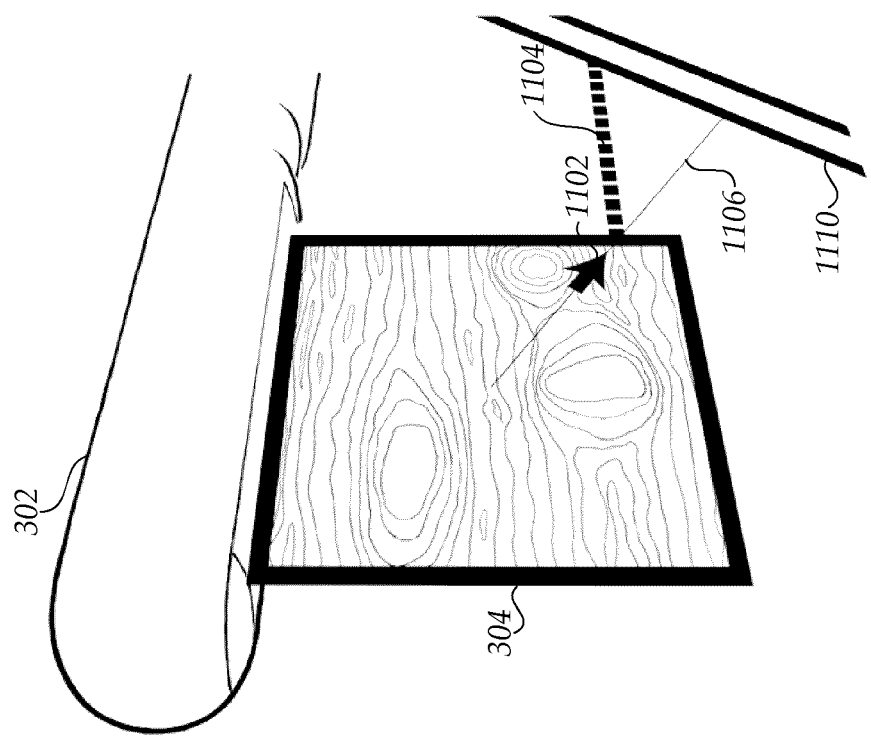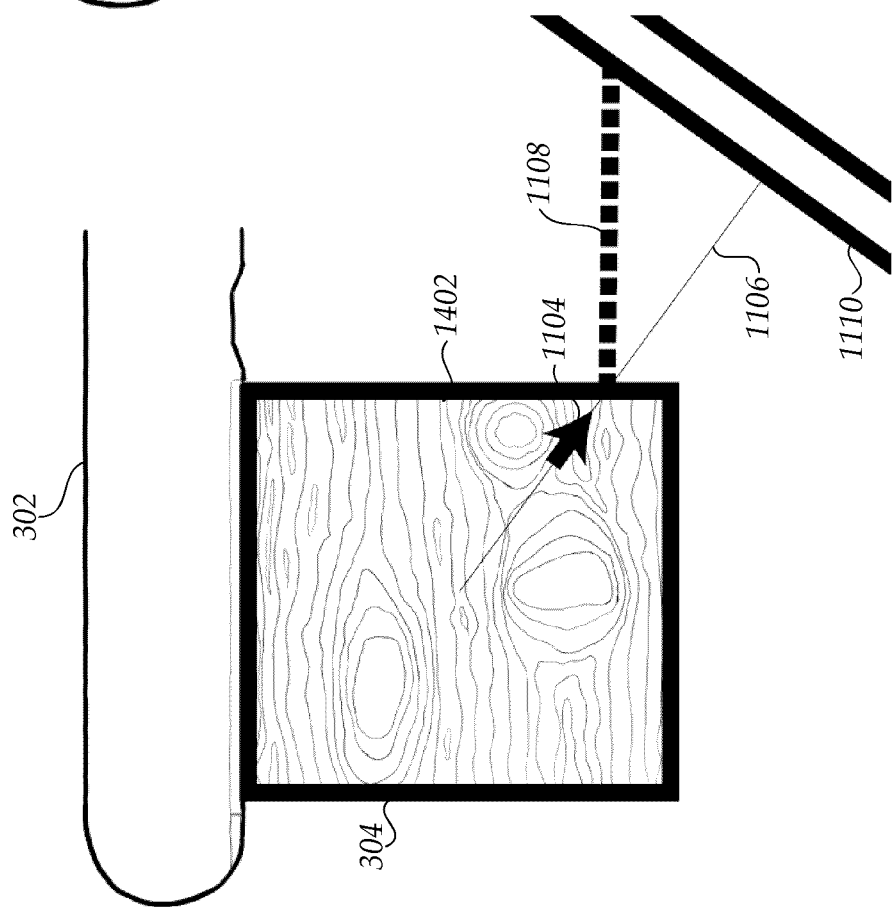
FIG. 11B
FIG. 11A

SURGICAL GUIDANCE INTERSECTION DISPLAY

CROSS-REFERENCE TO RELATED APPLICATIONS

The present application claims priority benefit to U.S. Provisional Application No. 62/091,238, which is hereby incorporated herein by reference in its entirety.

TECHNICAL FIELD

The systems and methods disclosed herein relate generally to computer systems facilitating medical device guidance through tissue by a medical practitioner.

BACKGROUND

Various medical device systems are available to aid a healthcare provider to guide a medical device in a patient. The medical device systems can provide various image guidance cues to aid the healthcare provider, and can also provide views of images of an imaged region and of virtual medical devices corresponding to physical medical devices.

BRIEF DESCRIPTION OF THE DRAWINGS

FIGS. 3A, 3B, 3C are diagrams of an embodiment illustrating various perspective views of a scene including at least one variance volume.

FIGS. 5A, 5B, and 5C are diagrams of an embodiment illustrating various perspective views of a scene including an elliptical intersection indicator.

FIGS. 6A, 6B, and 6C are diagrams of an embodiment illustrating various perspective views of a scene including an obround-shaped intersection indicator.

FIGS. 7A, 7B, and 7C are diagrams of an embodiment illustrating various perspective views of a scene including multiple intersection indicators.

FIGS. 10A and 10B are diagrams of an embodiment illustrating various perspective views of a scene including multiple display objects.

FIGS. 11A and 11B are diagrams illustrating an embodiment in which an intersection indicator is located outside an image region

DETAILED DESCRIPTION

Figure 1:
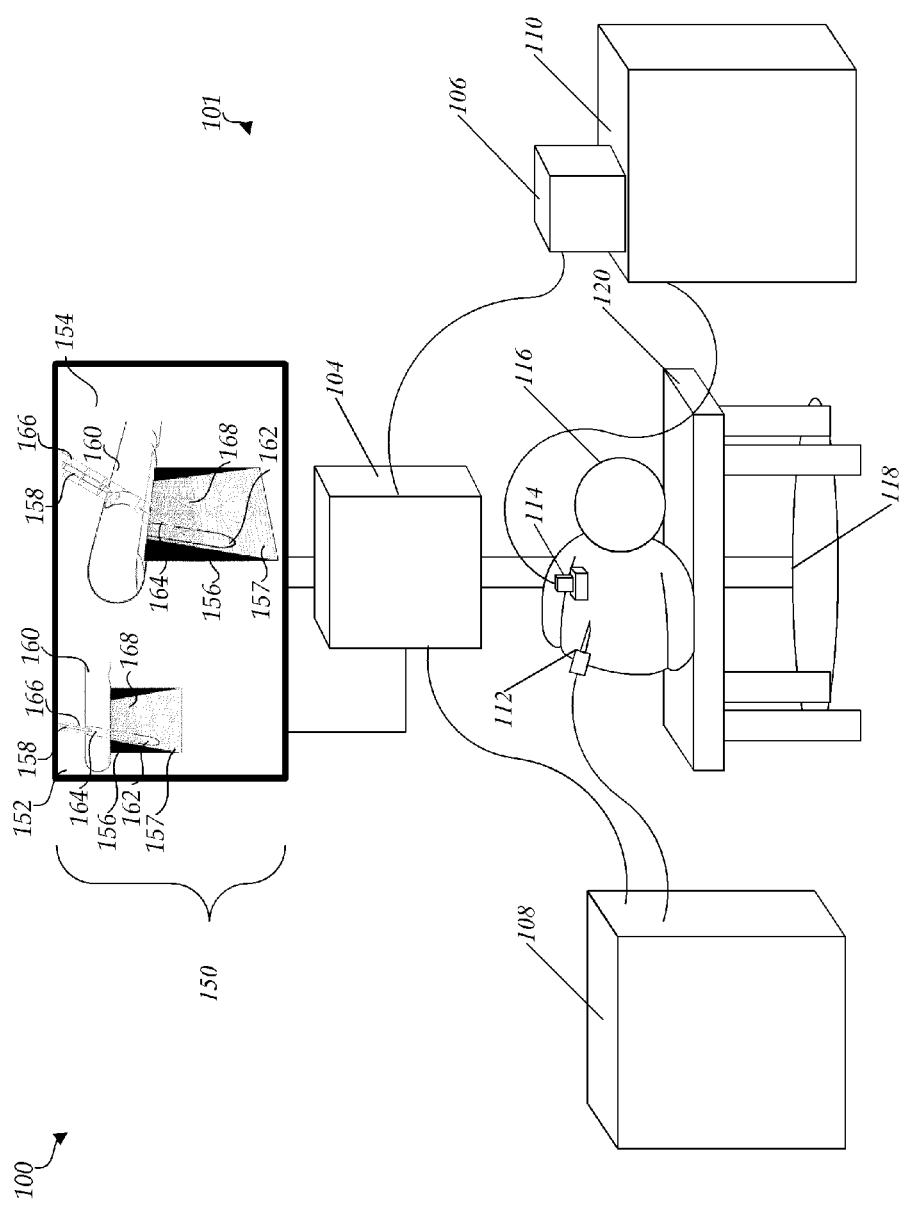
FIG. 1 is a diagram of an embodiment of a system for image-guided medical procedures.

Implementations disclosed herein provide systems, methods, and apparatus for generating images facilitating medical device insertion into tissue by an operator. Certain embodiments pertain to a free-hand medical device guidance system. The system can provide the healthcare provider manual control over the medical device, while making the spatial relationships between the target, medical device and U/S image more intuitive via a visual display. Using this visual feedback, the operator can adjust the medical device's position, orientation, or trajectory. Certain of the contemplated embodiments can be used in conjunction with systems described in greater detail in U.S. patent application Ser. No. 13/014,587, filed Jan. 26, 2011, entitled SYSTEMS, METHODS, APPARATUSES, AND COMPUTER-READABLE MEDIA FOR IMAGE MANAGEMENT IN IMAGE-GUIDED MEDICAL PROCEDURES; U.S. patent application Ser. No. 13/753,274, filed Jan. 29, 2013, entitled MULTIPLE MEDICAL DEVICE GUIDANCE (the '274 Application); U.S. patent application Ser. No. 14/212,933, filed Mar. 14, 2014, entitled MEDICAL DEVICE GUIDANCE; and U.S. patent application Ser. No. 14/872,930, entitled AFFECTED REGION DISPLAY, filed Oct. 1, 2015; each of which is hereby incorporated herein by reference in its entirety.

The system can aid the healthcare provider in guiding one or more medical devices through the tissue of the patient and/or placing the medical devices, and can be used for treatment of tumors, fibroids or cysts, with bipolar radiofrequency medical device ablation, multiple microwave medical devices, electroporation, and/or electrochemotherapy systems. It can also be used for nerve or muscle stimulation or sensing (electrodes in the spine, brain). The system can be used during open surgery, laparoscopic surgery, endoscopic procedures, biopsies, and/or interventional radiology procedures.

The system can be used in conjunction with live intraoperative ultrasound (U/S), pre-operative CT, or any cross-sectional medical imaging modality (e.g. MRI, OCT, etc.). In addition, the system can use a variety of techniques to determine the position and/or orientation of one or more medical devices. For example, the system can use the NDI Aurora magnetic system, the Ascension MedSafe system, a NDI Polaris optical system, etc. In some embodiments, a position sensor can be embedded inside, or affixed to each medical device, at the tip, along the shaft, and/or on the handle. Sensors can be built into the medical devices or attached after manufacturing, as described in greater detail in U.S. application Ser. No. 14/212,184, filed Mar. 14, 2014, entitled SENSOR MOUNT, incorporated herein in its entirety.

Each medical device can be associated with one or more sensors, which can continually, or repeatedly, report position and/or orientation, or a single sensor can be used for all the medical devices. In embodiments where one sensor is used, the healthcare provider can attach the sensor to the particular medical device that she is intentionally repositioning, and then, once she has placed that medical device, she can remove the sensor and attach it to the next medical device she is repositioning. In some embodiments, the medical devices can be manipulated by the healthcare provider. In certain embodiments, the system can be used with a robotic manipulator, where the robot controls the medical devices.

In some embodiments, the handles of medical devices can have push-button switches, to allow the user to select a medical device, indicate a tissue target, etc. The handle can also have an indicator light to indicate to the users which medical device is selected. Finally, the handle can have an encoder to detect how much length of electrode has been exposed by the user, and report this information to the guidance system and therapeutic generator Image Guidance Systems FIG. 1 is a diagram illustrating an embodiment of an environment 100 for image management in image-guided medical procedures. In the illustrated embodiment, the environment 100 includes a display 102 displaying an image 150, an image guidance unit 104, a position sensing unit 106, a surgical system 108, imager 110, surgical instruments 112, 155, a patient 116, a stand 118, and a table 120. In some embodiments, the image guidance system 101 can include any one or any combination of the display 102, the image guidance unit 104, the position sensing unit 106, the surgical system 108, the imager 110, the surgical instruments 112, 155, the stand 118, and/or the table 120.

In some embodiments, the position sensing unit 106 can track surgical instruments 112, 114, also referred to herein as medical devices 112, 114, within a tracking area and provide data to the image guidance unit 104. The medical devices 112, 114 can include invasive medical devices, such as, but not limited to, biopsy needles, ablation needles, surgical needles, nerve-block needles, or other needles, electrocautery device, catheters, stents, laparoscopes or laparoscopic cameras, ultrasound transducers, or other instruments that enter a part of the body, and non-invasive medical devices that do not enter the body, such as, but not limited to, ultrasound transducers, probes, or other external imaging devices, etc. The medical devices 112, 114 can also include medical imaging devices that provide or aid in the selection of medical images for display. In some embodiments, the medical imaging device can be any device that is used to select a particular medical image for display. The medical imaging devices can include invasive medical devices, such as laparoscopic cameras, and non-invasive medical devices, such as external ultrasound transducers.

Although only two surgical instruments 112, 114 are shown in FIG. 1, it will be understood that additional surgical instruments can be tracked and associated data can be provided to the image guidance unit 104. The image guidance unit 104 can process or combine the data and show image guidance data on display 102. This image guidance data can be used by a healthcare provider to guide a procedure and improve care. There are numerous other possible embodiments of system 101. For example, many of the depicted components can be joined together to form a single component and can be implemented in a single computer or machine. Further, additional position sensing units can be used in conjunction with position sensing unit 106 to track relevant surgical instruments 112, 114, as discussed in more detail below. Additional imagers 110 can be included, and combined imaging data from the multiple imagers 110 can be processed by image guidance unit 104 and shown on display 102. Additionally, two or more surgical systems 108 can be used.

Information about and from multiple surgical systems 108 and attached surgical instruments 112 (and additional surgical instruments not shown) can be processed by image guidance unit 104 and shown on display 102. These and other possible embodiments are discussed in more detail below. It will be understood that any combination of the display objects, image guidance cues, etc., described herein can be displayed concurrently, or simultaneously. Further, reference to displaying objects "concurrently" and/or "simultaneously" is to be interpreted broadly and may refer to displaying objects in such a way that to a human observer the objects are visible at the same time.

Imager 110 can be communicatively coupled to image guidance unit 104. In some embodiments, imager 110 can be coupled to a second display unit (not shown). The second display unit can display imaging data from imager 110. The imaging data displayed on display 102 and displayed on second display unit can be the same or different. In some embodiments, the imager 110 can be an ultrasound machine 110, the medical device 114 can be a movable imaging unit, such as an ultrasound transducer 114 or ultrasound probe 114, and the second display unit can be a display associated with the ultrasound machine 110 that displays the ultrasound images from the ultrasound machine 110. In some embodiments, a movable imaging unit 114 can be communicatively coupled to image guidance unit 104. The movable imaging unit 114 can be useful for allowing a user to indicate what portions of a first set of imaging data are to be displayed. For example, the movable imaging unit 114 can be an ultrasound transducer 114, a needle or other medical device, for example, and can be used by a user to indicate what portions of imaging data, such as a pre-operative CT scan, to show on a display 102 as image 150. Further, in some embodiments, there can be a third set of pre-operative imaging data that can be displayed with the first set of imaging data.

In some embodiments, a navigation system comprises a display 102 and a position sensing unit 106 communicatively coupled to image guidance unit 104. In some embodiments, position sensing unit 106, display 102, and image guidance unit 104 are coupled to the stand 118. Image guidance unit 104 can be used to produce images 150 that are displayed on display 102. The images 150 produced on display 102 by the image guidance unit 104 can be determined based on ultrasound or other visual images from the first surgical instrument 112 and second surgical instrument 114.

In the illustrated embodiment, the image 150 includes a 2D viewing area 152 and a 3D viewing area 154 (which can also be referred to as a virtual 3D space) each of which includes various display objects. In the 2D viewing area, some or all of the display objects can be displayed as 2D objects. However, it will be understood that some of the display objects in the 2D viewing area can be displayed as 3D objects. In the 3D viewing area 154, some or all of the display objects are displayed as 3D objects. Furthermore, the display objects in the 3D viewing area can be displayed in a perspective based at least in part on a point-of-view location. In the illustrated embodiment, the display objects include, an image region 156 with an ultrasound image 157, a virtual medical device 158 corresponding to the first surgical instrument 112, a virtual imaging device 160 corresponding to the second surgical instrument 114, intersection indicator 162, trajectory indicator 164, variance volume indicator 166, and shaded region 168. It will be understood that any combination of the aforementioned display objects can be displayed in the 2D viewing area and/or 3D viewing area as desired.

As a non-limiting example, if the first surgical instrument 112 is an ablation needle 112 and the second surgical instrument 114 is an ultrasound probe 114, then images 150 produced on display 102 can include the images, or video, from the ultrasound probe 114 (e.g., image slice 156) combined with other medical display objects and image guidance cues, such as projected medical device drive (e.g., trajectory indicators 164) or projected ablation volume (not shown), determined based on the emplacement of ablation needle 112. If the first surgical instrument 112 is an ultrasound probe 112 and the second surgical instrument 114 is a laparoscopic camera 114, then images 150 produced on display 102 can include the video from the laparoscopic camera 114 combined with ultrasound data superimposed on the laparoscopic image. More surgical instruments can be added to the system. For example, the system can include an ultrasound probe, ablation needle, laparoscopic camera, stapler, cauterizer, scalpel and/or any other surgical instrument or medical device. The system can also process and/or display collected data, such as preoperative CT scans, X-Rays, MRIs, laser scanned 3D surfaces etc.

The term "emplacement" as used herein is a broad term and may refer to, without limitation, position and/or orientation or any other appropriate location information. The term "pose" as used herein is a broad term encompassing its plain and ordinary meaning and may refer to, without limitation, position and orientation or any other appropriate location information. In some embodiments, the imaging data obtained from one or both of surgical instruments 112 and 114 can include other modalities such as a CT scan, MRI, open-magnet MRI, optical coherence tomography ("OCT"), positron emission tomography ("PET") scans, fluoroscopy, ultrasound, or other preoperative, or intraoperative 2D or 3D anatomical imaging data. In some embodiments, surgical instruments 112 and 114 can also be scalpels, implantable hardware, or any other device used in surgery. Any appropriate surgical system 108 or imager 110 can be communicatively coupled to the corresponding medical instruments 112 and 114.

As noted above, the images 150 produced can also be generated based on live, intraoperative, or real-time data obtained using the second surgical instrument 114, which is communicatively coupled to imager 110. The term "real time" as used herein is a broad term and has its ordinary and customary meaning, including without limitation instantaneously or nearly instantaneously. The use of the term real time can also mean that actions are performed or data is obtained with the intention to be used immediately, upon the next cycle of a system or control loop, or any other appropriate meaning. Additionally, as used herein, real-time data can be data that is obtained at a frequency that would allow a healthcare provider to meaningfully interact with the data during surgery. For example, in some embodiments, real-time data can be a medical image of a patient that is updated one time per second. In some embodiments, real-time data can be ultrasound data that is updated multiple times per second.

The surgical instruments 112, 114 can be communicatively coupled to the position sensing unit 106 (e.g., sensors embedded or coupled to the surgical instruments 112, 114 can be communicatively coupled with the position sensing unit 106). The position sensing unit 106 can be part of imager 110 or it can be separate. The position sensing unit 106 can be used to determine the emplacement of first surgical instrument 112 and/or the second surgical instrument 114. In some embodiments, the position sensing unit 106 can include a magnetic tracker and/or one or more magnetic coils can be coupled to surgical instruments 112 and/or 114. In some embodiments, the position sensing unit 106 can include an optical tracker and/or one or more visually-detectable fiducials can be coupled to surgical instruments 112 and/or 114. In some embodiments, the position sensing unit 106 can be located below the patient. In such embodiments, the position sensing unit 106 can be located on or below the table 120. For example, in embodiments where the position sensing unit 106 is a magnetic tracker, it can be mounted below the surgical table 120. Such an arrangement can be useful when the tracking volume of the position sensing unit 106 is dependent on the location of the position sensing unit 106, as with many magnetic trackers. In some embodiments, magnetic tracking coils can be mounted in or on the medical devices 112 and 114.

In some embodiments, the position sensing unit can determine one or more x, y, z coordinates and/or the quaternions (e.g., yaw, pitch, and/or roll) of device trackers associated with one or more of the medical devices 112, 114. In some embodiments, the position sensing unit 106 can be an electromagnetic measurement system (e.g., NDI Aurora system) using sensor coils for device trackers attached to the first and/or second surgical devices 112, 114. In some embodiments, the position sensing unit 106 can be an optical 3D tracking system using fiducials. Such optical 3D tracking systems can include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, the position sensing unit 106 can each be an inertial 3D tracking system comprising a compass, accelerometer, tilt sensor, and/or gyro, such as the InterSense InertiaCube or the Nintendo Wii controller. In some embodiments, the position sensing unit 106 can be attached to or affixed on the corresponding surgical device 112 and 114.

In some embodiments, the position sensing units 106, can include sensing devices such as the HiBall tracking system, a GPS device, or signal emitting device that would allow for tracking of the position and/or orientation (e.g., emplacement) of the device tracker (also referred to as an emplacement sensor). In some embodiments, a position sensing unit 106 can be affixed to either or both of the surgical devices 112, 114. The surgical devices 112 or 114 can be tracked by the position sensing unit 106. A room coordinate system reference, such as the display 102 can also be tracked by the position sensing unit 106 in order to determine the emplacements of the surgical devices 112, 114 with respect to the room coordinate system. Devices 112, 114 can also include or have coupled thereto one or more accelerometers, which can be used to estimate movement, position, and location of the devices.

In some embodiments, the position sensing unit 106 can be an Ascension Flock of Birds, Nest of Birds, driveBAY, medSAFE, trakSTAR, miniBIRD, MotionSTAR, pciBIRD, or Calypso 2D Localization System and device trackers attached to the first and/or second medical devices 112, 114 can be magnetic tracking coils.

The term "device tracker" (also referred to as an emplacement sensor), as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below. In some embodiments, the device trackers can be implemented using optical position sensing devices, such as the HiBall tracking system and the position sensing unit 106 can form part of the HiBall tracking system. Device trackers can also include a GPS device or signal emitting device that allows for tracking of the position and/or orientation of the device tracker. In some embodiments, a signal emitting device might include a radio-frequency identifier (RFID). In such embodiments, the position sensing unit 106 can use the GPS coordinates of the device trackers or can, for example, triangulate the radio frequency signal being emitted by the RFID associated with device trackers. The tracking systems can also include one or more 3D mice.

Furthermore, the system 101 can use the emplacement data associated with the device trackers (e.g., received from the device trackers or from the position sensing unit 106) to determine other emplacement information, including, but not limited to the emplacement of a trajectory, an image plane, image region, imaged region, and/or one or more intersections, etc. The determined emplacement information can be used to generate and display the various image guidance cues, such as, but not limited to, the intersection indicator 162, the trajectory indicator 164, the variance volume 166, the shaded region 168, the image region 156 with the image 157, etc.

In some embodiments, the imaged region can correspond to the tissue or region that is imaged (area and/or volume) by the medical device 114. In some cases, the image plane can correspond to the plane at which the medical device 114 acquires an image and/or a plane in the virtual 3D space that is associated therewith. In certain cases, the image region can correspond to the region (area and/or volume) at which the medical device 114 acquires an image and/or to a region in the virtual 3D space associated therewith. For example, in some cases, image data acquired by the medical device 114 in the medical device's image region can be mapped to a corresponding virtual image region in the virtual 3D space. The image region may also be referred to as an image slice and/or image slab. Furthermore, in some embodiments, the image region can include at least a portion of the image plane.

The emplacement of the image plane, image region (area and/or volume), and/or imaged region can also be determined based at least in part on the operating parameters of the medical device 114. For example, the operating parameters can indicate what portion of the medical device 114 will capture an image (e.g., emit ultrasonic waves), as well as the dimensions of the image region and/or imaged region (e.g., height, width, and/or depth of the image that will be acquired), as well as the image region.

Images 150 can be produced based on intraoperative or real-time data obtained using first surgical instrument 112, which is coupled to first surgical system 108. In the illustrated embodiment of FIG. 1, the first surgical system 108 is shown as coupled to image guidance unit 104. The coupling between the first surgical system 108 and image guidance unit 104 may not be present in all embodiments. In some embodiments, the coupling between first surgical system 108 and image guidance unit 104 can be included where information about first surgical instrument 112 available to first surgical system 108 is useful for the processing performed by image guidance unit 104. For example, in some embodiments, the first surgical instrument 112 can be an ablation needle 112 and first surgical system 108 can be an ablation system 108. In some embodiments, it can be useful to send a signal about the relative strength of planned ablation from ablation system 108 to image guidance unit 104 so that the image guidance unit 104 can show a predicted ablation volume. In other embodiments, the first surgical system 108 is not coupled to image guidance unit 104. Example embodiments including images and graphics that can be displayed are included below.

In some embodiments, the display 102 displays 3D images to a user, such as a healthcare provider. Stereoscopic 3D displays separate the imagery shown to each of the user's eyes. This can be accomplished by a stereoscopic display, a lenticular auto-stereoscopic display, or any other appropriate type of display. The display 102 can be an alternating row or alternating column display. Example alternating row displays include the Miracube G240S, as well as Zalman Trimon Monitors. Alternating column displays include devices manufactured by Sharp, as well as many "auto-stereoscopic" displays (e.g., Philips). In some embodiments, Sony Panasonic 3D passive displays and LG, Samsung, and/or Vizio 3D TVs can be used as well. Display 102 can also be a cathode ray tube. Cathode Ray Tube (CRT) based devices, can use temporal sequencing, showing imagery for the left and right eye in temporal sequential alternation. This method can also be used projection-based devices, as well as by liquid crystal display (LCD) devices, light emitting diode (LED) devices, and/or organic LED (OLED) devices.

In certain embodiments, the display 102 can be a head mounted display (HMD) worn by the user in order to receive 3D images from the image guidance unit 104. In such embodiments, a separate display, such as the pictured display 102, can be omitted. The 3D graphics can be produced using underlying data models, stored in the image guidance unit 104 and projected onto one or more 2D planes in order to create left and right eye images for a head mount, lenticular, or other 3D display. The underlying 3D model can be updated based on the relative emplacements of the various devices 112 and 114, as determined by the position sensing unit(s) 106, and/or based on new data associated with the devices 112 and 114. For example, if the second medical device 114 is an ultrasound probe, then the underlying data model can be updated to reflect the most recent ultrasound image. If the first medical device 112 is an ablation needle, then the underlying model can be updated to reflect any changes related to the needle, such as power or duration information. Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

One or more components, units, devices, or elements of various embodiments can be packaged and/or distributed as part of a kit. For example, in one embodiment, an ablation needle, one or more device trackers, 3D viewing glasses, and/or a portion of an ultrasound wand can form a kit. Other embodiments can have different elements or combinations of elements grouped and/or packaged together. Kits can be sold or distributed separately from or with the other portions of the system.

One will readily recognize that there are numerous other examples of image guidance systems which can use, incorporate, support, or provide for the techniques, methods, processes, and systems described herein.

Depicting Surgical Instruments

It can often be difficult to discern the content of a 3D scene from a 2D depiction of it, or even from a 3D depiction of it. Therefore, various embodiments herein provide image guidance that can help the healthcare provider better understand the scene, relative emplacements or poses of objects in the scene and thereby provide improved image guidance.

Figure 2:
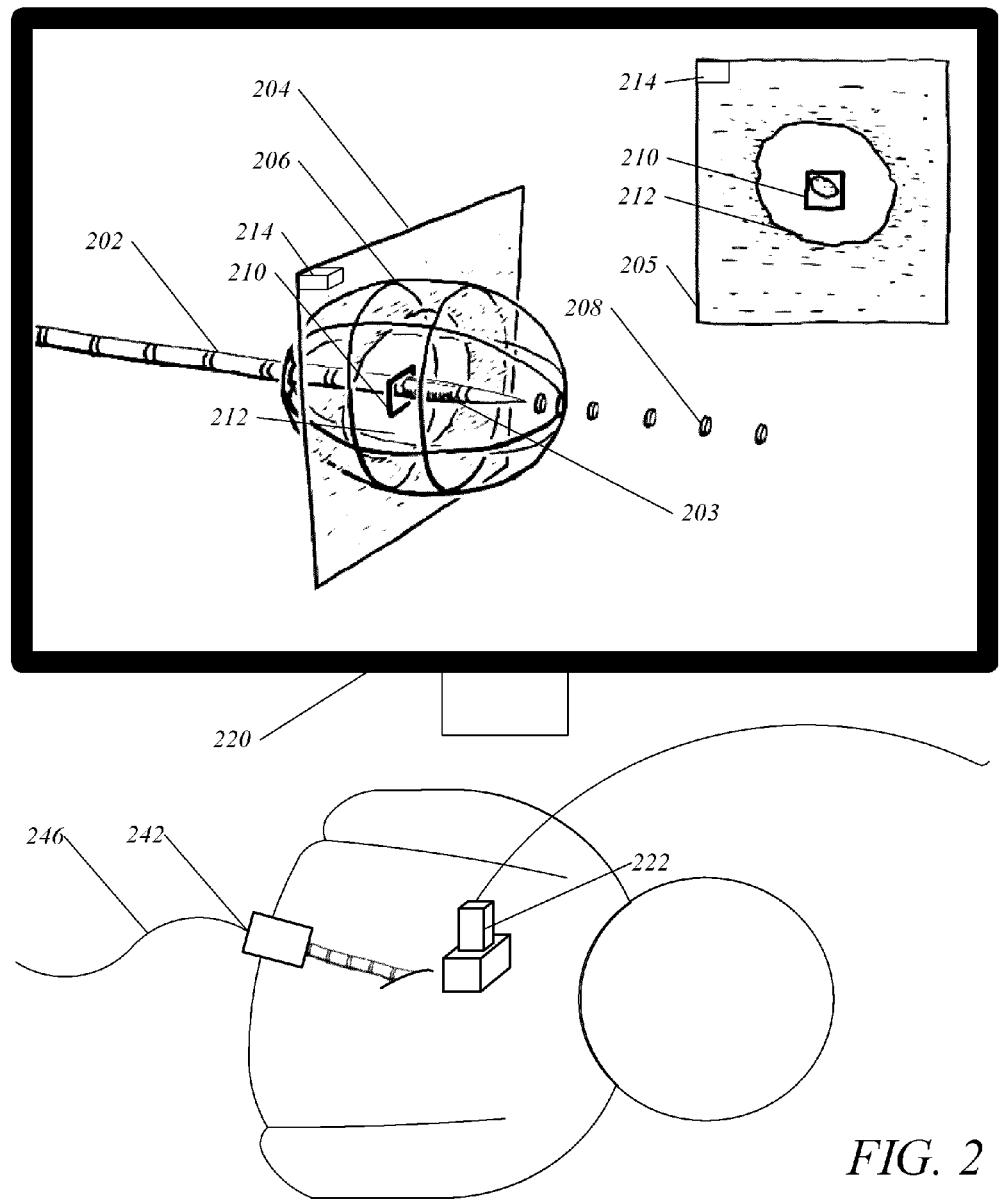
FIG. 2 is a diagram of an embodiment of a rendering of image guidance cues and medical display objects on a display.

FIG. 2 illustrates a perspective view of a virtual rendering 202 of a surgical instrument 242 being displayed on a screen 220 with a perspective view of a medical image 204. In some embodiments, the screen 220 can correspond to the screen of the display 102, which can be implemented using a TV, computer screen, head-mounted display, projector, etc. In the illustrated embodiment, the rendered surgical instrument 202 displayed on the screen 220 corresponds to the ablation needle 242. A wire 246 connecting the ablation needle 242 to an ablation system (not shown) is also depicted in FIG. 2.

Although only one virtual surgical instrument 202 is displayed, it will be understood that multiple medical devices can be tracked and displayed concurrently, or simultaneously, on screen 220, as described in greater detail in the '274 Application, previously incorporated by reference. For example, a virtual rendering of the medical imaging device 222 can be displayed.

The virtual surgical instrument 202 can be displayed in a virtual 3D space with the screen 220 acting as a window into the virtual 3D space. Thus, as the surgical instrument 242 is moved to the right with respect to a point-of-view location (e.g., the location of the point-of-view for viewing the 3D space), the virtual surgical instrument 202 can also move to the right. Similarly, if the surgical instrument 242 is rotated 90 degrees so that the tip of the surgical instrument is pointing away from the point-of-view location (e.g., at the screen 220), the virtual surgical instrument 201 will likewise show the change in orientation, and show the tip of the virtual surgical instrument 202 in the background and the other end of the virtual surgical instrument 202 in the foreground. In some embodiments, as described in greater detail in U.S. application Ser. No. 14/212,933, incorporated herein by reference in its entirety, the point-of-view location can be a fixed location, such as a predetermined distance/angle from the screen 220 or stand 118 and or a location configured by the user; or the point-of-view location can by dynamic. For example, the system can track a user in real-time and determine the point-of-view location based at least in part on the tracked location of the user.

Some models of medical devices have markings such as bands around the shaft (to indicate distance along the shaft), and a colored region 203 near the tip to indicate from where the radio frequency or microwave energy is emitted in the case of an ablation probe. Healthcare providers performing medical device procedures are often familiar with these markings and can use them to help understand the spatial relationship between the medical device and anatomy. In some embodiments, the make and model of the medical device 242 is known to the image guidance system and the virtual medical device 202 displayed in display 220 can resemble medical device 242. The features of medical devices that can be rendered in the scene include the overall shape (diameter, cross sectional shape, curvature, etc.), color, distance markers, visuals or echogenic fiduciary markers, the state of deployable elements such as tines, paddles, anchors, resection loops, stiffening or steerable sleeves, temperature, radiation, light or magnetic field sensors, lens, waveguides, fluid transfer channels, and the like.

The type of medical device being used can be input into the image guidance system 101, can be a system default, can be detected by a camera or other device, can be received as data from an attached medical device, such as surgical system 108 in FIG. 1, or the information can be received in any other appropriate manner. Displaying on display 220, a virtual surgical instrument that resembled the surgical instrument 242 can help healthcare providers associate the image guidance data with the real world and can provide more familiar guidance information to a healthcare provider, thereby further aiding the healthcare provider in the guidance task. For example, the healthcare provider can see the familiar markings on the medical device being displayed on the display 220 and therefore be familiar with the distance and relative placement of the displayed medical device with respect to other data, such as a tumor 212 seen in a rendered ultrasound image 204, 205. This knowledge of relative placement of items being displayed can help the healthcare provider move the medical device 242 into place.

Consider an embodiment in which the virtual surgical instrument 202 in the display 220 is an ablation needle depicting the portion of the needle that will perform the ablation, for example, the portion that emits the radio or microwave energy. If the display 220 also includes ultrasound data, then the doctor can be able to find the tumor 212 she wishes to ablate by moving the ultrasound probe around until she spots the tumor 212. In various embodiments, she will be able to see the displayed ultrasound data and its location relative to the displayed medical device with the markings. She can then drive the medical device until she sees, on display 220, that the emitter-portion of the medical device encompasses the tumor in the ultrasound, also seen on display 220. When she activates the ablation, she can then be more certain that she has ablated the correct portion of the tissue. Various embodiments of this are discussed below.

As another example, consider the physical markings that can be on the instruments themselves. These markings can help orient a healthcare provider during use of the instrument. In some embodiments, the image guidance unit can represent these markings in the images displayed in the display. For example, certain ultrasound transducers are built with an orientation mark (e.g., a small bump) on one side of the transducing array. That mark can also be shown in the ultrasound image on the scanner's display, to help the healthcare provider understand where the scanned anatomical structures shown on screen are located under the transducer, inside the patient. In some embodiments, the image guidance system can display a symbolic 3D representation of the orientation mark both next to the motion-tracked ultrasound slice (e.g., moving with the displayed ultrasound slice) and next to the 2D view of the ultrasound slice also displayed by the system. An example of this is displayed in FIG. 2, where a small rectilinear volume 214 corresponding to a feature on an ultrasound probe is shown both in proximity to the ultrasound slice displayed in the 3D view and the ultrasound slice displayed in a 2D view.

It will be understood that an image slice or image slab can also refer to image data received from an imaging device, such as an ultrasound transponder. In some embodiments, the image data can correspond to a cross-section of tissue having a certain thickness. In some instances, the imaging device can compact the image data, and/or treat the image data as 2D data, such that there is no perceived thickness. In certain embodiments, when the image slice is displayed in a 3D view, the system can treat the image slice as a 2D or quasi 2D object. In such embodiments, the system can cause the image slice to have little to no perceptible thickness. Accordingly, in certain embodiments, when the image slice is oriented orthogonally or perpendicularly with respect to the point-of-view location, the system can cause the display to display nothing or a line having a relatively small thickness, such as a few pixels, etc. In some cases, the number of pixels used to display the relatively small thickness of the image slice can correspond to the size of the display. For example, more pixels can be used for a larger display and fewer pixels can be used for a smaller display, etc.

Other embodiments can track and display other types of instruments and their features. For example, a healthcare provider may want to track one or more of a scalpel, a biopsy, a cauterizer (including an electrocauterizer and Bovies), forceps, cutting loops on hysteroscopes, harmonic sheers, lasers (including $CO_2$ lasers), etc. For example, in various embodiments, the following devices can be tracked and various aspects of their design displayed on display 220: Olympus™ OES Pro Hystero-Resectoscope, SonoSurg Ultrasonic Surgical System Olympus™ GF-UC 160 Endoscope Wallus™ Embryo Transfer Catheter AngioDynamics® NanoKnife™, VenaCure™ laser, StarBurst, Uniblade, Habib® Resector Bovie™ Electrodes, Covidien Evident™, Cool-tip™ Ablation Antennas, Opti4™ Electrodes Microsulis MEA (microwave endometrial ablation), Acculis Halt™ Medical System Optimed BigLumen Aspiration Catheter Optimed Optipure Stent Central venous catheterization introducer medical device (such as those made by Bard and Arrow).

Once tracked, a healthcare provider is able to see image guidance data on display 220 that will allow her to know the relative pose, location, or emplacement of the tracked instrument(s) with respect to one another or with respect to imaging data and will be able to see, on display 220, the features of the instrument rendered in the scene.

Depicting Medical Device Placement, Trajectory, and Other Image Guidance Cues

In certain procedures, the system can provide image prediction information related to the surgical instruments as image guidance cues. In the context of scalpel movement, this can be the location that the scalpel will hit if a healthcare provider continues to move the scalpel in a particular direction. In the context of ablation or biopsies, this can be the projected medical device placement if it is driven along its central axis, which is also referred to herein as a longitudinal axis.

FIG. 2 further illustrates an embodiment of a projected needle drive 208 (also referred to as a trajectory indicator) as an image guidance cue. If a healthcare provider is driving an ablation needle 242 into tissue (not pictured), then she can know where the medical device will be driven. In some embodiments, the projected drive 208 of a medical device can be depicted on the display 220 and can show the healthcare provider the projected path 208 that the medical device 242 will take if it is driven along its central axis. Although the trajectory of only one medical device is displayed, it will be understood that the trajectory of multiple medical devices can be determined and displayed simultaneously on screen 220, as described in greater detail in the '274 Application.

In some embodiments, to implement the trajectory indicators 208, the image guidance system can draw a number of rings about the axis of the medical device shaft, extrapolated beyond its tip, as depicted in FIG. 2. A healthcare provider can view and manipulate the emplacement of the medical device 242 and its expected drive projection (via its displayed projected trajectory) before it enters the patient's tissue. In some embodiments, this is accomplished by the doctor positioning the virtual rings in the drive projection such that they are co-incident (or pass through) the ultrasound representation of a target, such as a tumor that the doctor has spotted in the ultrasound. This can allow the healthcare provider to verify that the medical device 242 is properly aimed at the target and can drive the medical device 242 forward into the tissue such that it reaches its desired target or destination. For example, if the doctor identifies a tumor 212 in the ultrasound image, she can align the ablation needle 242 such that the drive projection rings on display 220 intersect or otherwise indicate that the medical device, if driven straight, will reach the tumor 212.

The rings can, in some embodiments, be spaced at regular (e.g., 0.5, 1, or 2 cm) intervals to provide the healthcare provider with visual or guidance cues regarding the distance from the medical device tip to the targeted anatomy. In some embodiments, the spacing of the rings can indicate other aspects of the data, such as the drive speed of the medical device, the density of the tissue, the distance to a landmark, such as the ultrasound data, or any other appropriate guidance data or property. In some embodiments, the rings or other trajectory indicators can extend beyond the medical device tip, by a distance equal to the length of the medical device-shaft. This way, the user knows if the medical device is long enough to reach the target—even before the tip enters the patient. That is, in some embodiments, if the rings do not reach the target with the tip still outside the body, then the tip will not reach the target even when the entire length shaft is inserted into the body.

Other display markers can be used to show trajectory, such as a dashed, dotted, or solid line, transparent medical device shaft, point cloud, wire frame, etc. In some embodiments, three-dimensional rings can be used and provide depth cues and obscure little of the ultrasound image. Virtual rings or other virtual markers can be displayed semi-transparently, so that they obscure less of the ultrasound image than an opaque marker would.

Other prediction information can also be displayed as image guidance cues. For example, if a scalpel is being tracked by the image guidance system, then a cutting plane corresponding to the scalpel can be displayed (not pictured). Such a cutting plane can be coplanar with the blade of the scalpel and can project from the blade of the scalpel. For example, the projected cutting plane can show where the scalpel would cut if the doctor were to advance the scalpel. Similar prediction information can be estimable or determinable for cauterizers, lasers, and numerous other surgical instruments.

Furthermore, the data from two or more devices can be combined and displayed based on their relative emplacements or poses. For example, the rendered ultrasound image 204 can be displayed on the image plane (e.g., in the image region) with respect to the virtual medical device 202 on the display 220 in a manner that estimates the relative emplacements or poses of the medical imaging device 222 and the medical device 242. As illustrated in FIG. 2, the image guidance cues associated with the virtual medical device 202, including the affected region indicator 206 and trajectory indicators 208, are shown spatially located with the rendered ultrasound image 204 on display 220.

In addition, the display 220 can include another image guidance cue in the form of an intersection indicator 210 that indicates where the virtual ablation medical device 202 (and/or its axis and/or its trajectory) intersects the ultrasound image 204. In some embodiments, the intersection indicator 210 can be displayed before the medical device is inserted, thereby allowing the healthcare provider to see where the medical device will intersect the image, or imaged region. As will be described in greater detail below, in some cases, due to uncertainties related to the emplacement of the medical devices, the system can use a variance parameter to determine and display the intersection indicator 210.

In the illustrated embodiment, a tumor 212 appears in the ultrasound image, or rendered ultrasound image 204, and the virtual ablation needle 202 is shown driven through the tumor 212. As described in greater detail in U.S. application Ser. No. 14/872,930 (the '930 Application), incorporated herein by reference in its entirety, the displayed affected region (or affected region indicator) 206 can indicate what region or volume would be affected when the medical device 242 is operated. In the illustrated embodiment, the displayed affected region 206 can estimate where ablation would occur if the tissue were ablated at that time. As can be seen, in the illustrated embodiment, the displayed affected region 206 appears to cover the tumor displayed in the ultrasound image.

It will be understood that the various embodiments described herein for using a variance parameter associated with a device tracker to determine and display an intersection indicator can also be used to determine and display the displayed affected region 206. Furthermore, the variance parameters described herein can be used alone or in combination with the various variance parameters described in the '930 Application to determine and display the affected regions described therein, including the surface display regions.

Various embodiments can include any combinations of the graphics described above and/or other graphics or image guidance cues. For example, in some embodiments, data related to a single surgical instrument (such as an ablation needle, ultrasound probe, etc.) can be presented in more than one manner on a single display. Consider an embodiment in which device 242 is an ablation needle and device 222 is an ultrasound transducer. As mentioned previously, as the medical devices are displayed in a virtual 3D space, with the screen 220 acting as a window into the virtual 3D space, if a healthcare provider orients medical imaging device 222 such that it is perpendicular to the point-of-view or point-of-view location (e.g., perpendicular to the screen), the perspective view of the ultrasound image 204 would show only the edge and the contents of the ultrasound image 204 would not be visible. In some embodiments, the image guidance system can track the healthcare provider's head using an emplacement sensor and/or a position sensing unit. In some embodiments, such as, when the head of a user is tracked, the healthcare provider can then move her head to the side, so that she sees the ultrasound image from a different point of view location.

In some embodiments, the image guidance system can concurrently display an additional 2D view 205 of the ultrasound image, simultaneous to the 3D depiction 204, so that the ultrasound image is always visible, regardless of the emplacement in which the healthcare provider holds the medical imaging device 222. The 2D view 205 of the ultrasound data can be similar to what a healthcare provider is accustomed to seeing with traditional ultrasound displays. This can be useful to provide the healthcare provider with imaging to which she is accustomed and allows a healthcare provider to see the ultrasound data regardless of the then-current emplacement of the ultrasound probe with respect to the user.

In some embodiments, the 2D view 205 of an ultrasound image is depicted in the upper right corner of the monitor (though it can be placed in any location). In some embodiments, the guidance system can automatically (and continually) choose a corner in which to render the 2D view 205 of the ultrasound image, based on the 3D position of the surgical instruments in the rendered scene. For example, in FIG. 2, ablation needle 242 can be held in the healthcare provider's left hand and the medical device shaft is to the left of the 3D view of the ultrasound image slice, so that the 2D view 202 of the ultrasound image in the upper right corner of display 220 does not cover any of the 3D features of the medical device (or vice-versa). If the medical device were held in the healthcare provider's right hand (and to the right of the ultrasound image 204, the virtual medical device shaft would appear on the right side. To prevent the 2D view 205 in the corner of display 220 from covering the medical device shaft, the system can automatically move it to a corner that would not otherwise be occupied by graphics or data.

In some embodiments, the system 101 attempts to avoid having the 2D view 205 of the ultrasound image quickly moving among corners of the display in order to avoid overlapping with graphics and data in the display. For example, a function f can be used to determine which corner is most suitable for the 2D ultrasound image to be drawn in. The inputs to f can include the locations, in the screen coordinate system, of the displayed medical device tip, the corners of the 3D view of the ultrasound image, etc. In some embodiments, f s output for any given point in time is independent of f's output in the previous frames, which can cause the ultrasound image to move among corners of the display rapidly. In some embodiments, the image guidance system will filter f's output over time. For example, the output of a filter g, for any given frame, could be the corner, which has been output by f the most number of times over the last n frames, possibly weighting the most recent values for f most heavily. The output of the filter g can be used to determine in which corner of display 220 to display the 2D ultrasound image and the temporal filtering provided by g can allow the 2D view 205 of the ultrasound image display to move more smoothly among the corners of the display 220.

In some embodiments, other appropriate virtual information and/or image guidance cues can be overlaid on the 2D view 205 of the ultrasound image as well as the 3D view 204. Examples include: orientation indicator 214, an indication of the distance between the medical device's tip and the point in the plane of the ultrasound image that is closest to the medical device tip; the cross section or outline of the ablation volume that intersects with the ultrasound slice; and/or the intersection point, box, outline, etc. between the virtual medical device's axis and the ultrasound image plane.

Furthermore, it will be understood that other image guidance cues can be generated and displayed on the display as described in greater detail in the '274 Application, previously incorporated herein by reference. For example, the system 101 can generate and/or display graphical indicators that help indicate the spatial relationship between a medical device and an ultrasound image plane (e.g., graphical image plane indicators) or other plane indicators to indicate the relative positions of the virtual medical device(s) and ultrasound image, features of interest, annotations, foundational plane indicators, foundational plane intersection indicators, other graphical indicators, approximate medical device location indicators, etc. As described in greater detail above and in the '274 Application, the various image guidance cues can be generated based at least in part on the emplacement information of the medical devices used with the system 101.

Figures Overview

FIGS. 3A-3C, 5A-5C, 6A-6C, 7A-7C, 10A, 10B, 8A, 8B, 9A-9C, 10A, 10B, 11A, and 11B are diagrams of embodiments illustrating various perspective views of scenes including various display objects. The scenes depicted therein can be displayed as part of the images 150 and/or on the screen 220. For example, the scenes depicted in FIGS. 3A, 5A, 6A, 7A, 9A 10A, and 11A can represent embodiments illustrating display objects that can be displayed in the 2D viewing area 152 and/or in the 3D viewing area 154 when the medical imaging device corresponding to virtual medical device 302 (and/or its image plane/region) is at least approximately parallel with respect to a point-of-viewlocation. The scenes depicted in FIGS. 3B, 5B, 6B, 7B, and 9B can represent embodiments illustrating display objects that can be displayed in the 3D viewing area 154 when the medical imaging device corresponding to virtual medical device 302 (and/or its image plane/region) is at least approximately orthogonal or perpendicular with respect to the point-of-view-location. The scenes depicted in FIGS. 3C, 5C, 6C, 7C, 8A, 8B, 9C, 10B, and 11B can represent embodiments illustrating display objects that can be displayed in the 3D viewing area 154 when the medical imaging device corresponding to virtual medical device 302 (and/or its image plane/region) is neither parallel nor orthogonal with respect to the point-of-view-location. In addition, similarly numbered display objects across the figures correspond to similar display objects.

Furthermore, it will be understood that any one or any combination of the display objects shown in the figures can be displayed alone or in combination with any one or any combination of the display objects shown in other figures. For example, in some embodiments, only an intersection indicator or variance volume indicator is displayed on the screen 220. In certain embodiments, only an intersection indicator and at least one of the virtual medical imaging device or virtual medical device are displayed on the screen 220, etc.

Emplacement Variance

In some cases, there can be some uncertainty as to the precise emplacement of the tracked medical device 242. For example, a device tracker associated with the medical device can have some error or variance associated with it (e.g., 5%-10%). The variance may be due to noise, jitter, vibration, manufacturing and/or mechanical tolerances involved when affixing the pose sensor to the medical devices. The variance may result in the precise emplacement of the medical device being different than the emplacement of the virtual medical device displayed on the screen 220.

In some cases, the operating parameters of a device tracker can include one or more emplacement variance parameters indicating the amount of variance that a healthcare provider can expect when using a particular device tracker. The emplacement variance parameter may indicate a percentage certainty of the location of the device tracker (non-limiting examples: 95% or 99%) and/or may indicate that a device tracker operates within a certain range, or that a healthcare provider can expect a certain variance in location, such as a particular standard deviation and/or +/− some percent. For example, the emplacement variance parameter may indicate that the location of the device tracker is in a particular location with an error of one or more millimeters or 5%-10%, etc.

In some embodiments, the system can account for some uncertainty about the spatial relationship between the virtual medical device and the image plane/region using the variance parameter. For example, in some embodiments, the system models, the medical device, not as just a one-dimensional axis, but as a three dimensional tube, with a diameter that is related to the accuracy of the tracking system (accuracy can be based on measurement error, noise, jitter, vibration, due attributable to the user and/or attributable to the pose sensor). Similarly, in certain embodiments, the system can model the image plane/region as a three-dimensional slab, with a thickness that is related to the accuracy of the system. The system can use the uncertainty to generate and display to the user graphic indicators (analogous to error-bars on a scientific plot), such as a variance volume indicator, intersection indicator, etc.

FIGS. 3A-3C are diagrams of an embodiment illustrating various perspective views of a scene including a variance volume. In the illustrated embodiments of FIGS. 3A-3C, the display objects include a virtual medical imaging device 302, an image region (displayed as an image area) 304 that includes an ultrasound image, a virtual medical device 306, a trajectory indicator 308, a variance volume indicator 310, image width indicators 312a, 312b, and image slab 314.

It will be understood that any one or any combination of the display objects shown in FIGS. 3A-3C can be displayed alone or in combination as desired. For example, in some embodiments, only the variance volume indicator 310 is displayed on the screen 220. In certain embodiments, only the variance volume 310 and the virtual medical device 306 are displayed on the screen 220, etc.

To determine and display the virtual medical imaging device 302, the system 101 can use emplacement data associated with a medical imaging device that corresponds to the virtual medical imaging device 302 and/or dimensions of the medical imaging device. The system 101 can use the dimensions to determine the shape and dimensions of the virtual medical imaging device 302 and/or can use the emplacement data to determine the emplacement of the virtual medical imaging device 302. Using the emplacement data associated with the medical device that corresponds to the virtual medical device 306 and/or dimensions of the medical imaging device, the system 101 can determine and display the virtual medical device 306.

Similarly, the system 101 can use the emplacement data associated with the medical imaging device and/or its operating parameters to determine and display the image region 304. For example, the system 101 can use the operating parameters (e.g., height, length, width) to determine, the shape and dimensions of the image region and/or can use the emplacement data to determine the emplacement of the image region 304. In addition, as imaging data is received from the medical imaging device, the system 101 can combine the imaging data with the image region 304, as illustrated in FIGS. 3A, 3B. For example, the system 101 can map the imaging data from one coordinate system to an image region 304 coordinate system and/or the display coordinate system. It will be understood that although reference throughout is made to displaying the image region as an image area, the image region can be displayed as an image volume.

Image width indicators 312a, 312b and image slab 314 are shown in FIGS. 3B, 3C to illustrate a thickness of the image region/imaged region that corresponds to the image data displayed in the image region 304 and may or may not be displayed as part of the image 150. The image width indicators 312a, 312b can correspond to different planes or different areas of the image slab 314, image volume, or imaged region. The shape and dimensions of the image width indicators 312a, 312b can be associated with, or correspond to, the shape of the image region 304 and/or the shape of an image generated by the medical device 302. Image width indicator 312a can correspond to a proximal width (e.g., a portion of the width that is closer to the point-of-view location than the image region 304) and image width indicator 312b can correspond to a distal width (e.g., a portion of the width that is further from the point-of-view location than the image region 304). Of course, it will be understood that the proximal and distal width indicators can change depending on the orientation of the medical device/virtual medical device. Image slab 314 can correspond to the image region and/or the image region between the image width indicators 312*a*, 312*b* and can include the image region 304.

As mentioned above, medical imaging devices often capture a cross-section of tissue having a certain thickness. However, in some instances, a medical imaging device treats the captured cross-section as if there is no thickness and compacts the image data so that there is no perceived thickness in the image data. The image width indicators 312*a*, 312*b* and/or image slab 314 can be used to illustrate a width of the imaged region that corresponds to the image data that is shown in the image region 304, prior to the image data being compressed. In addition, the image width indicators 312*a*, 312*b* and/or image slab 314 can be used to determine one or more intersection indicators as described in greater detail below with reference to FIGS. 6A-6C and 7A-7C. Similar to the image region 304, the image width indicators 312*a*, 312*b* and/or image slab 314 can be determined and displayed based at least in part on the emplacement data and/or the operating parameters associated with the virtual medical imaging device 302. It will be understood that although the image width indicators 312*a*, 312*b* in the illustrated embodiment correspond to the ends of the image region, that any plane or planes of the image slab 314 or image region can be used to determine and display the image indicator 710.

To determine the variance volume, the system 101 can use a determined axis of the virtual medical device 306 and the variance parameters. For example, the system 101 can calculate a volume surrounding the axis based at least in part on the variance parameter. Once determined, the system 101 can cause a variance volume indicator 310 to be displayed on the screen 220.

In some embodiments, to display the variance volume indicator 310, the system 101 can determine the emplacement of the virtual medical device based at least in part on the emplacement data associated with a medical device and display variance volume indicator based at least in part on the determined emplacement of the virtual medical device. In some cases determining the emplacement of the virtual medical device can include receiving x, y, z and/or quaternion orientation coordinates associated with a device tracker that is associated with the medical device and mapping the received coordinates to display coordinates associated with the screen 220. Once the emplacement of the virtual medical device is determined, the system 101 can determine the variance volume as a volume surrounding the medical device and/or the axis of the medical device. To display the variance volume indicator 310 (and/or any display object described herein), the system 101 can communicate the coordinates of the variance volume (and/or any display object described herein) to a graphics rendering engine, which can convert the emplacement data to display coordinates and communicate the resulting rasterized image to a display buffer, which is then converted to a video signal (e.g. DVI/HDMI) and sent to a display screen 220.

In the illustrated embodiment, the variance volume indicator 310 is displayed using multiple, equally-spaced rings surrounding and along the axis of the virtual medical, as well as two lines illustrating the perimeter of the variance volume. In this way, the variance volume indicator 310 appears to be made up of multiple cylinders stacked on top of one another. However, it will be understood that the variance volume indicator 310 can be displayed in a variety of ways, as desired. For example, the rings may not be equally-spaced or not included at all. Similarly, the perimeter lines may be omitted. In some embodiments, the variance volume indicator 310 can be displayed as a long tube along the axis of the virtual medical device. The tube can be shaded or textured as desired.

The variance volume can also be drawn as animated bars that rotate about the center of the medical device axis. In some embodiments, the longitudinal axis of the bars can be parallel to the longitudinal axis of the medical device. In certain embodiments, the longitudinal axis of the bars can be at an angle with respect to the longitudinal axis of the medical device (e.g., perpendicular, forty-five degrees, or any other angle). Each bar can be a predetermined length that spans the entire medical device or just a portion thereof. Furthermore, there can be multiple sets of rotating bars at different locations along the medical device. Each set of rotating bars along the axis can include one or more bars. For example, in some embodiments, there can be three sets (each set located at a different position along the medical device) of three bars each. It will be understood that any number of sets of bars can be used and that each set can include any number of bars.

In some embodiments, the variance parameter can be fixed such that the variance volume does not change. In certain embodiments, the variance parameter may change over time. In such embodiments, the variance volume and the variance volume indicator can change over time as well. In some embodiments, the variance parameter may not be uniform for the length of the needle. In such embodiments, the variance volume indicator 110 can indicate the different variance parameters along the medical device. Furthermore, although the variance parameter has been described with respect to the virtual medical device 306, it will be understood that a variance parameter associated with the virtual medical device 302 can be used alone or in combination with the variance parameter associated with the virtual medical device 306. The variance parameter associated with the virtual medical device 302 can be used to determine the emplacement of the virtual medical device 302 and medical device associated therewith and to display a variance volume associated with the virtual medical device 302. Accordingly, more than one variance parameter can be used by the system 101 to determine emplacement of the virtual medical devices 302, 206 and display them on the screen 220.

Figure 4:
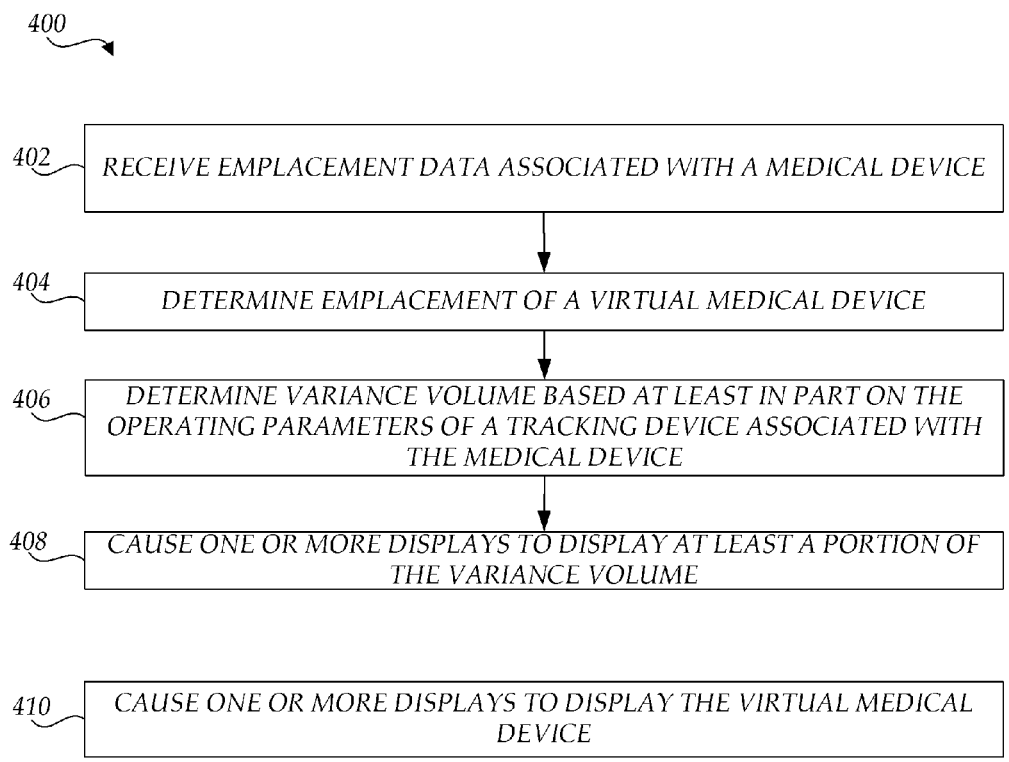
FIG. 4 is a flow diagram illustrative of an embodiment of a routine implemented by the system to display the variance volume.

FIG. 4 is a flow diagram illustrative of an embodiment of a routine 400 implemented by the system 101 to display at least a portion of a variance volume or a variance volume indicator. One skilled in the relevant art will appreciate that the elements outlined for routine 400 can be implemented by one or more computing devices/components that are associated with the system 101, such as the position sensing unit 106, the image guidance unit 104, surgical system 108, and/or the imager 110. Accordingly, routine 400 has been logically associated as being generally performed by the system 101. However, the following illustrative embodiment should not be construed as limiting. Furthermore, it will be understood that the various blocks described herein with reference to FIG. 4 can be implemented in a variety of orders. For example, the system may implement some blocks concurrently or change the order, as desired.

At block 402, the system 101 receives emplacement data associated with a medical device. In some embodiments, the emplacement data can be received from a device tracker associated with the medical device and/or a position sensing unit 106. In certain embodiments, the emplacement data includes emplacement coordinates, such as, but not limited to one or more x, y, z position coordinates and/or quaternion orientation coordinates.

At block 404, the system 101 determines emplacement of a virtual medical device associated with the medical device. In some embodiments, the system 101 uses the emplacement data associated with the medical device to determine the emplacement of the virtual medical device. In certain embodiments, the system 101 determines the emplacement by converting the emplacement coordinates corresponding to a coordinate system of the position sensing unit 106 to a coordinate system corresponding to a display. In some embodiments, the system 101 can use dimensions of the medical device (e.g., length, circumference, etc.) to determine the emplacement of the virtual medical device. The system 101 can include a non-transitory computer-readable medium that stores the dimensions of various medical devices that can be used with the system and/or receive the dimensions from the medical device or elsewhere dynamically.

At block 406, the system 101 can determine a variance volume based at least in part on one or more operating parameters associated with the device tracker that is associated with the medical device. In some embodiments, the operating parameters can include a location variance parameter. In some embodiments, the system 101 can use a determined axis of the virtual medical device and the variance parameter to determine the variance volume. In certain embodiments, the system 101 can use the trajectory of the virtual medical device and/or the dimensions of the virtual medical device to determine the variance volume.

At block 408, the system 101 can cause one or more displays to display a variance volume indicator or at least a portion of the variance volume, as described in greater detail above. In some embodiments, the variance volume indicator can correspond to at least a portion of the variance volume that intersects with an image region, as will be described in greater detail below with reference to FIGS. 5A-5C. In such embodiments, the variance volume indicator can also be referred to as an intersection indicator.

In some embodiments, to cause the one or more displays to display the variance volume indicator (and/or any of the display objects described herein), the system 101 can communicate the emplacement data of the variance volume (and/or display object) to graphics rendering engine, which can convert the emplacement data to display coordinates and communicate the resulting rasterized image to a display buffer, which is then converted to a video signal (e.g. DVI/HDMI) and sent to a display screen 220.

It will be understood that fewer, more, or different blocks can be used as part of the routine 400. For example, in some embodiments, the system 101 can cause the one or more displays to display the virtual medical device as illustrated at block 410 and described in greater detail above. Furthermore, the blocks of routine 400 can be combined with any one or more of the blocks described below with reference to FIGS. 12 and 13.

Intersection Indicator

The emplacement variance can also affect the certainty with regard to the emplacement of an intersection between the imaged region and the medical device. FIGS. 5A-5C are diagrams of an embodiment illustrating various perspective views of a scene including display objects. In the illustrated embodiments of FIGS. 5A-5C, the display objects include the virtual medical imaging device 302, an image region 304 that includes a medical image, a virtual medical device 306, a trajectory indicator 308, an intersection indicator 510, image width indicators 312a, 312b, and image slab/region indicator 314.

To determine the intersection indicator 510, the system 101 can use the emplacement data associated with the medical device and the medical imaging device. The system can determine the intersection in the display coordinate system and/or the coordinate system of the position sensing unit 106. For example, the system 101 can determine an intersection of the trajectory and/or axis of the medical device and the image plane/region and/or the imaged region and/or an intersection of the trajectory and/or axis of the virtual medical device with the image plane/region. In addition, the system can determine the intersection of an axis associated with the first emplacement data, or first emplacement data axis, and a plane associated with the second emplacement data, or second emplacement data plane. For simplicity, reference is made to determining an intersection of the image plane/region and the virtual medical device 302, however, it will be understood that other methods can be used to determine an intersection of the image plane/region or imaged region and an axis of the medical device.

In some embodiments, to determine the intersection, the system 101 can compare the various coordinates of the two objects (e.g., axis/trajectory and region/plane). If a pair of coordinates (e.g., the x, y, z coordinates from each object) match (e.g., are equal) or satisfy a distance threshold, the system can determine that the two objects intersect. In certain embodiments, the system 101 can determine that there is an intersection if the trajectory/axis of the virtual medical device 302 and a portion of the image plane/region can be mapped to the same pixels in a video or image output data buffer.

The distance threshold can be a predefined distance, such as one or more bits, one or more pixels, etc. In some embodiments, the distance threshold can be based at least in part on whether the distance between the coordinates is perceptible to a user, which may be based at least in part on the size of the display, the size of the display relative to the image and/or imaged region, and/or the distance between the point-of-view location and the display, etc. For example, in some cases, the distance threshold can be smaller for larger displays (or larger display:image ratios) and larger for smaller displays (or smaller display:image ratios), or vice versa. In certain cases, the distance threshold can be larger for larger distances between the point-of-view location and the display and smaller for smaller distances between the point-of-view location and the display, or vice versa. In certain embodiments, the distance threshold can be different for each coordinate.

In certain embodiments, the system 101 can perform the comparison for each location along the axis of the virtual medical device and/or image plane/region. In some cases, the system can determine that there is an intersection if the axis/trajectory of the virtual medical device and a portion of the image plane/region are level and have the same depth.

As mentioned above, any coordinate system can be used to compare the coordinates of the virtual medical device with the image plane/region and/or to determine whether the virtual medical device and the image plane/region intersect. For example, the coordinate system of the display and/or the coordinate system of position sensing unit 106 can be used as desired.

In some embodiments, for each location on the display, the system can query whether a portion of the two display objects have been (or will be) mapped to that location. If the system 101 determines that a portion of two display objects (e.g., the trajectory of the virtual medical device and the image region have been (or will be) mapped to that location, the system 101 can determine that the two display objects intersect. In certain embodiments, the system 101 can determine that the two display objects satisfy the location threshold and/or intersect if the two objects map to the same location on a display, such as the same pixel or same array of pixels.

In some embodiments, the system 101 can determine the intersection indicator based at least in part on the determined intersection of the axis of the virtual medical device and the image region and a variance parameter associated with the device tracker associated with the virtual medical device. For example, once the intersection is determined, the system 101 can use the variance parameter to generate an area on the image region 304 that represents the potential location of intersection. In some cases, the center of the area can correspond to the determined point of intersection.

In some embodiments, the system 101 can determine and/or display the 3D shape that results from the intersection of the slab containing the image plane (e.g., the volume between the image width indicators 312a, 312b), and the variance volume containing the medical device axis (illustrated as a cylinder surrounding the medical device and its trajectory, with multiple circles at regular (or irregular) intervals). This can be drawn, transparently composited, with the image and medical device or medical device trajectory.

In certain embodiments, the system 101 can use the intersection of a determined variance volume with the image plane/region to determine the intersection indicator. For example, the area or perimeter of the variance volume that intersects with the image plane/region can be used as the intersection indicator. Such an embodiment is illustrated in FIGS. 5A and 5C. In the illustrated embodiment, the shape of the intersection indicator 510 is ellipsoid, however, it will be understood that any shape can be used as desired. For example, the shape can be rectilinear, as shown and described in greater detail below with reference to FIGS. 9A-9C and/or can include two parallel line segments connected by semi-circular end caps (obround shape), as shown and described in greater detail below with reference to FIGS. 6A-6C and 7A-7C.

Orientation Angle

In some embodiments, the system 101 can use an orientation angle or angle-of-approach to determine and display the intersection indicator 510. The orientation angle or angle-of-approach can correspond to the angle between the image plane and the medical device axis and/or the virtual medical device axis.

As the angle-of-approach decreases (e.g., the medical device is moved closer to being parallel with the image plane), the potential point(s) of intersection increase. Accordingly, in some embodiments, the system 101 can use the angle-of-approach to determine and display the intersection indicator. In certain embodiments, when the orientation angle satisfies a threshold angle, the intersection indicator can be deactivated.

In some embodiments, the system 101 can generate a 3D intersection shape described above and/or generate an intersection shape based on the intersection of the variance volume and the image plane/region, project it onto the image plane, and draw its outline on the image plane. For example, if the medical device (or virtual medical device) axis is at a 90-degree angle-of-approach to the image plane, the system can draw a hollow circle. As illustrated in FIGS. 5A-5C, as the angle-of-approach is reduced, the circle can become an ellipse. The minor diameter of the ellipse can correspond to the circle's (related to the accuracy of the system), whereas the major diameter can be related to the angle-of-approach.

As the angle becomes shallower, the ellipse's major diameter can become greater. Furthermore, some of the various figures included herein show differently sized intersection indicators, which, in some, embodiments, can be due to a different angle-of-approach.

Additionally, when the angle-of-approach becomes zero (or approximately zero), the major axis becomes infinite, and the intersection indicator can become two parallel lines, which can be unbounded. A non-limiting example is shown in FIGS. 11A and 11b, in which the intersection indicator 1110 is shown as two parallel lines. A non-limiting benefit of this embodiment is that it visually obscures less of the image region than a 3D intersection-indicator shape. In addition, when the clinician is approaching in-plane, or at shallow angles-of-approach, the parallel lines do not jump or move erratically, and the clinician can use it by manipulating the medical device and U/S probe such that the target is in between the two parallel lines, and, in this arrangement, she can determine that the medical device will hit the target if she maintains this orientation while driving the medical device forward into the tissue. This intersection-indicator smoothly can transition from two parallel lines to a circle, as the angle-of-approach changes.

In some embodiments, the system 101 can compare the orientation of the axis of the medical device or virtual medical device with the orientation of the image plane/region. Based on the comparison, the system 101 can increase or decrease the size of the intersection indicator. In some embodiments, as the angle between the orientations decreases (moves towards parallel), the size of the intersection indicator can increase. In certain embodiments, when the angle between the orientations is equal or approximately equal, the intersection indicator can be displayed as two parallel lines, which can be unbounded parallel lines.

Obround Intersection Indicator

FIGS. 6A-6C are diagrams of an embodiment illustrating various perspective views of a scene including a trajectory indicator having an obround shape. As shown in FIGS. 6A-6C, the shape of the intersection indicator 610 can be obround. The shape can be achieved by displaying a rounded edge on two sides with two parallel lines connecting the rounded edges. In some embodiments, the length of the parallel line segments can correspond to the angle-of-approach and/or with the major diameter of the elliptical intersection-indicator mentioned above. By using parallel and circular line segments (projected onto the image plane), the system can make it easier for the user to understand the angle between the image plane and the display surface of the screen 220 (via the perspective foreshortening effect).

In some embodiments, the system can use the intersection of the axis of the virtual medical device with multiple planes of the image region or image slab to determine and display the intersection indicator. FIGS. 7A-7C are diagrams illustrating an embodiment for determining and displaying a trajectory indicator using the image region or slab. As mentioned above, in some embodiments, the system 101 can generate a 3D intersection shape described above and/or generate an intersection shape based on the intersection of the variance volume and the image region (or image slab), project it onto the image plane, and draw it (or its outline) on the image plane as the intersection indicator 710.

The intersection indicator 710 can be determined in a variety of ways using the image region/slab 314. In some embodiments, the intersection shape can be based on the intersection of the variance volume across the image region or slab 314 and in certain embodiments, the intersection shape can be determined based on the intersection of the variance volume with one or more planes within the image region/slab 314.

For example, in some cases, the intersection indicator 710 can be based at least in part on the intersection of the variance volume with the image width indicator 312a (displayed as intersection indicator 712a), with the image width indicator and 312b (displayed as intersection indicator 712b), and with the image region 304 (displayed as intersection indicator 712c). Combining or projecting the three intersection indicators 712a, 712b, 712c onto the image region 304 can result in the intersection indicator 710 displayed on image region 304. In some cases, as part of the projecting, the rounded portions of the indicators 712a, 712b, 712c between the distal rounded portions can be removed.

In some embodiments, the intersection indicator 710 can be based on only the intersection indicators 712a and 712b and/or can omit determining the intersection of the variance volume with the image plane 304. In such embodiments, when the intersection indicators 712a and 712b are projected onto the image region 304, lines can be drawn between the distal rounded edges to generate the intersection indicator 710. As mentioned above, in some cases, as part of the projecting, the rounded portions of the indicators 712a, 712b between the distal rounded portions can be removed.

Device-Blocking-Objects

Figure 8B:
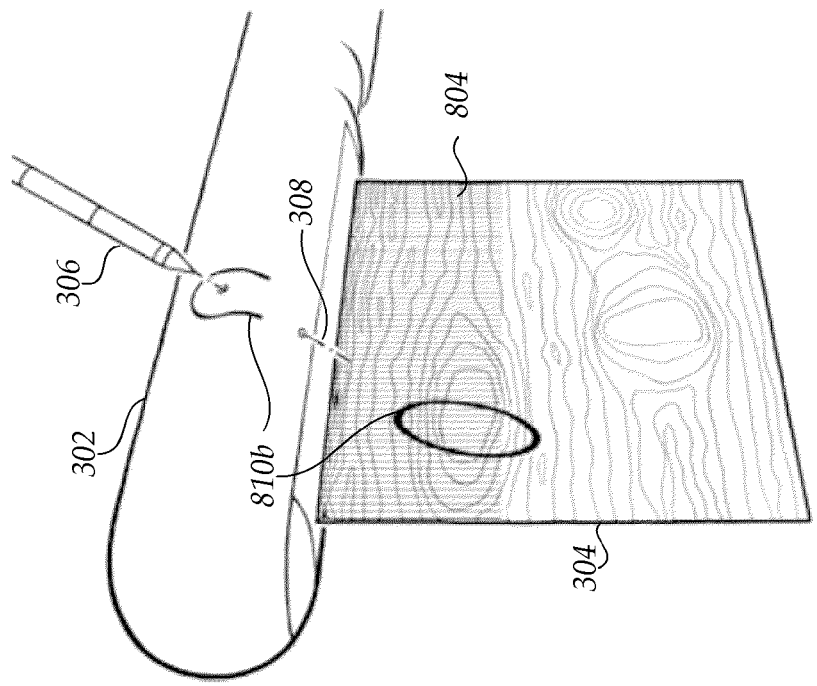
FIGS. 8A and 8B are diagrams of embodiments illustrating views of different scenes including an intersection indicator.
Figure 8A:
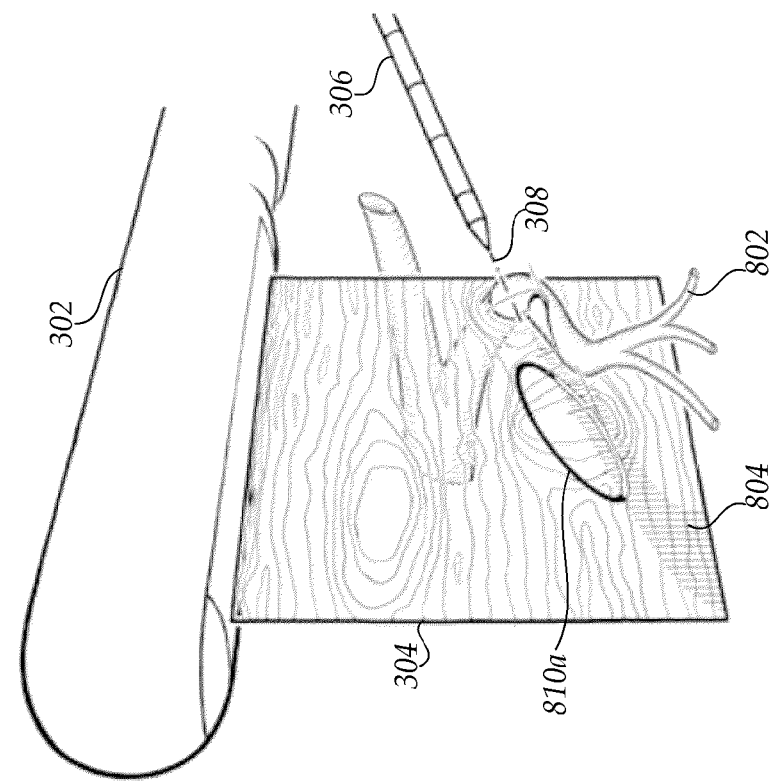

FIGS. 8A and 8B are diagrams of embodiments illustrating an intersection indicator for a scene intersecting with device-blocking display objects. In addition to determining intersections between an axis of the medical device and the image plane/region and displaying associated intersection indicators, the system 101 can also determine and display the intersection indicator 810a, 810b when the axis intersects with other display objects. For example, in some situations, the trajectory of the medical device 306, on its way to the image plane, might be blocked by objects or 3D structures that the clinician wishes to avoid hitting. Examples include the housing of the medical device associated with the virtual medical device 302, blood vessel 802, nerves, ribs or other bones, etc., which can be referred to generally as device-blocking-objects. FIG. 8A is a diagram illustrating an embodiment of an intersection indicator being 810a displayed on portions of the virtual medical device 302 and FIG. 8B is a diagram illustrating an embodiment of an intersection indicator 810b being displayed on portions of a blood vessel 802.

Based on emplacement data associated with these device-blocking-objects, the system can display corresponding display objects in their proper spatial arrangement with the image plane and the virtual medical device. The emplacement data can be received from device trackers, position sensing units 106, and/or based on 3D image data, such as a registered CT, MRI, etc. Using the emplacement data associated the device-blocking-objects and the medical device, the system 101 can determine any intersections. Based on the determined intersections, the system 101 can project the intersection indicator onto the surfaces of the device-blocking-blocking display objects. In some embodiments, the system 101 can determine which objects are device-blocking-objects by determining that an object intersects with the axis or variation volume of the medical device and the intersection is located between the medical device and an intersection of the medical device and the image region.

In addition, portions of the intersection indicator on the image plane that are blocked by a device-blocking object can be a different color, grayed out, or not drawn. For example, portions of the intersection indicator 810a that are blocks by the blood vessel 802 are displayed differently than portions of the intersection indicator 810a that are not blocked by the blood vessel 802. In this way, the system 101 can convey to a user that the device will not reach the target seen in the image region (if the medical device trajectory is not changed), which device-blocking-objects are in the way, which portions of them are in the path of the medical device, and if the medical device trajectory is barely or nearly blocked (since the intersection indicator has some width, diameter related to the accuracy of the system).

With respect to FIG. 8A, the system 101 can determine that the trajectory (and/or variance volume) of the medical device associated with the virtual medical device 306 intersects with a portion of the blood vessel 802. The emplacement data for the blood vessel can be based on an emplacement registered 3D image, such as a registered CT scan, MRI, CAT scan, etc. Based on the determined intersection, the system 101 can cause a display to display at least a portion of the intersection indicator onto the blood vessel 802. To draw the intersection indicator 810a onto the blood vessel, the system 101 can rely on the emplacement data of the blood vessel.

FIG. 8A further illustrates a shaded region 804 to indicate how portions of the image region 304 may not be accessible without going through the device-blocking-objects. In the illustrated embodiment, using the emplacement data of the image region 304 and the emplacement data of the blood vessel 802, the system 101 can determine a shaded region 804 based on which portions of the image region 304 are blocked by the blood vessel 802. The system can then display the shaded region 804 to indicate to a user the portions of the image region 304 that are not accessible based on the current position and/or orientation of the medical device. For example, the shaded region 804 can indicate what portions of the image region 304 are not accessible so long as the current position of the medical device is maintained and/or even if the current orientation of the medical device is adjusted.

Similar to FIG. 8A, FIG. 8B illustrates an embodiment in which portions of the image region 304 are blocked by a device-blocking-object. In the illustrated embodiment of FIG. 8B, the device-blocking-object is the virtual medical device 302. Based on a determined intersection of the axis and/or the variance volume of the virtual medical device 306 with the virtual medical imaging device 302, the system 101 can display a portion of the intersection indicator 810a, 810b on the virtual medical imaging device 302. In addition, based on a determination that a portion of the image region 304 is not accessible based on the current position and orientation of the medical device with respect to the image region, the system 101 can display a shaded region 804 that corresponds to the portions of the image region 304 that are not accessible.

FIGS. 8A and 8B further illustrate that, in some embodiments, the size and shape of the intersection indicators 810a, 810b can vary based at least in part on the emplacement of the virtual medical device 206 with respect to the image region. For example, as described in greater detail above, the size of the intersection indicator can change in relation to a changed orientation angle between the medical device and image region. In the illustrated embodiments of FIGS. 8A and 8B, the intersection indicator 810a is larger and more elongate than the intersection indicator 810b, which can be due in part to a smaller orientation angle between the medical device and image region in the embodiment illustrated in FIG. 8A compared to the orientation angle in the embodiment illustrated in FIG. 8B.

Figure 9C:
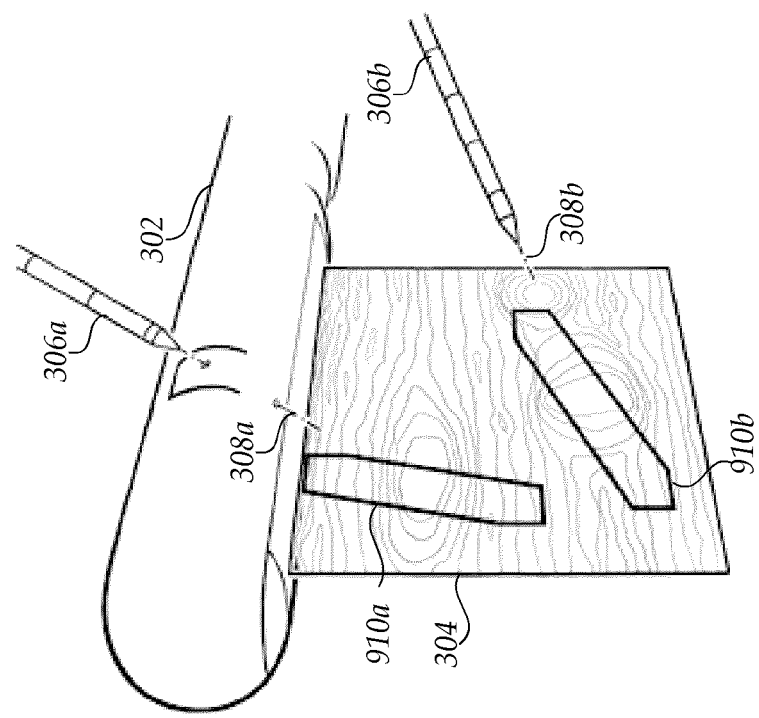
FIGS. 9A, 9B, and 9C are diagrams of an embodiment illustrating various perspective views of a scene including multiple intersection indicators associated with different virtual medical devices.
Figure 9B:
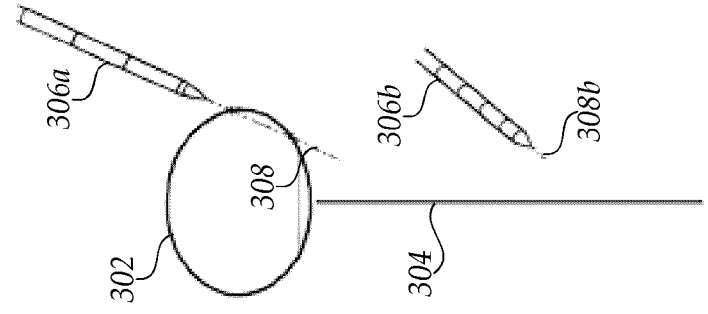
Figure 9A:
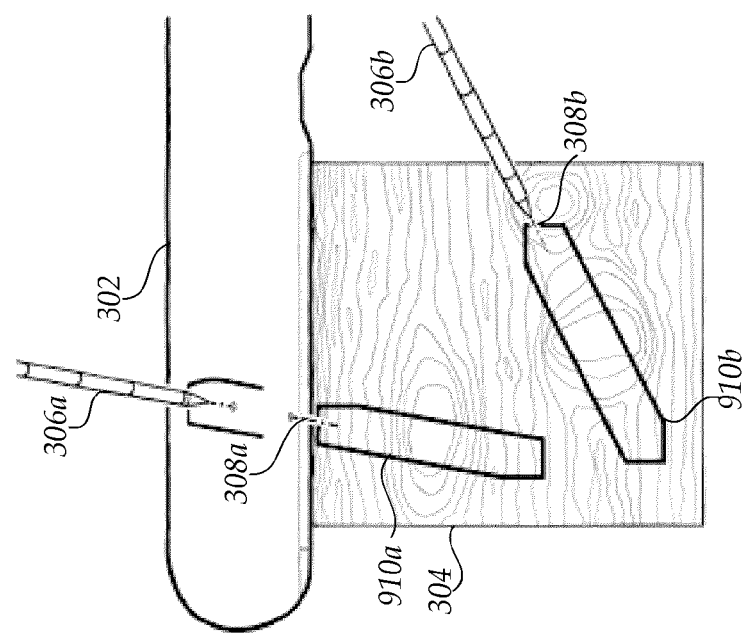

FIGS. 9A-9C are diagrams of an embodiment illustrating various perspective views of a scene including multiple intersection indicators 910a, 910b corresponding to different medical devices 306a, 306b. In the illustrated embodiment, the intersection indicators 910a, 910b are illustrated as rectilinear. In some embodiments, the corners of the intersection indicators can be drawn such that they have one or more line segments which are parallel to the edges of the image region 304. In this way, a user can more easily distinguish the intersection indicators 910a, 910b from other display objects, and can understand that the intersection indicator exists in the same plane as the image region 304.

The rectilinear display objects 910a, 910b can be determined similar to the determination of the intersection indicators described above with reference to FIGS. 5A-5C, 6A-6C, 7A-7C, 8A, and 8B. For example, the rectilinear intersection indicators can be determined based at least in part on an intersection of a first emplacement data axis with at least a portion of an image region and/or other display objects. In the illustrated embodiment, the system determines that the axis of the virtual medical device 306a intersects with the virtual medical device 302 and at least a portion of the image region, and the intersection indicator 910a is drawn on the virtual medical device 302 and in the image region 304. In addition, in the illustrated embodiment, the system determines that the axis of the virtual medical device 306b intersects with at least a portion of the image region and the image indicator 910b is displayed in the image region 304.

Image Region and Medical Device Image Difference

FIGS. 10A, 10B are diagrams of an embodiment illustrating various perspective views of a scene including multiple display objects. As mentioned previously, any one or any combination of the embodiments described herein can be displayed concurrently. FIGS. 10A, 10B depict embodiments in which many of the display objects described above with respect to FIGS. 3A-3C, 5A-5C, 6A-6C, 7A-7C, 8A, and 8B, are illustrated. For example, FIGS. 10A, 10B illustrate a virtual medical imaging device 302, an image region 304 displayed as an image area that includes a medical image 1002, a virtual medical device 306, a trajectory indicator 308, a variance volume indicator 310, a shaded region 804, and an intersection indicator 1010 intersecting with the virtual medical imaging device 302 and the image region 304.

In some embodiments, the medical image to be displayed on the image region may not match the size and/or shape of the image region 304, as illustrated in FIGS. 10A, 10B. For example, the image region 304 may be rectangular and the medical image 1002 may not be rectangular (e.g. it can be a convex scan and/or trapezoidal) and/or the image region 304 may be larger than the medical image 1002. In such embodiments, the system can bound the medical image 1002 with the image region 304 and/or or superimpose a grid or grid points over the medical image 1002 and/or image region 304, to help the user understand the orientation of the medical image and/or image region in the 3D context. In certain embodiments, the area outside the medical image 1002 and inside the image region 304 can be colored (e.g., black) differently from the medical image 1002 to distinguish it from the medical image 1002.

In some embodiments, the system 101 can compare the dimensions of the medical image 1002 with the dimensions of the image region 304. In certain embodiments, the dimensions can be stored in a non-transitory computer-readable medium associated with the system 101 and/or can be received from the medical imaging device, etc. Upon determining that the compared dimensions are different, the system 101 can identify the portions of the image region 304 that are outside, or do not overlap with, the medical image 1002. When displaying the image region 304 and the medical image 1002, the system 101 can display the portions of the image region 304 that overlap with the medical image 1002 with the medical image 1002 and can display the portions of the image region 304 outside, or that do not overlap with, the medical image 1002 differently to highlight the difference from the medical image 1002.

Off-Image Region Intersection

FIGS. 11A and 11B are diagrams illustrating an embodiment in which an intersection indicator is located outside the image region. In some embodiments, the system 101 can determine that the intersection indicator would be located outside of the image region (e.g., the intersection of the axis or variance volume of the medical device and the image plane is outside the image region) and/or outside the region of the display screen. When this happens, the system may draw one or more visual elements that indicate to the user, that the intersection indicator is outside the image region and/or off-screen.

The visual elements can include, as non-limiting examples, any one or any combination of changing the border of the image region 304 to be thicker 1102, and/or a different color (e.g. add a thick red border); altering the display of the image region 304 (increasing brightness, contrast); altering the display of the entire scene (e.g., displaying a border around the scene or changing the background of the display objects, etc; displaying a warning sign; displaying an arrow 1104 indicating in which direction the intersection indicator 1110 lies (e.g., the arrow 1104 may be overlaid/superimposed onto the image region 304, or drawn just beyond the border of the image region 304); displaying the numerical distance between the intersection indicator and the image region 304 (e.g., measured from the center of the image region 304, from a border of the image region 304, or other location); and/or displaying one or more lines connecting the intersection indicator to a portion of the image region's border (line 1106) or to the center of the image region 304 (line 1108), to visually indicate the intersection-indicator's location to the user, as also described in U.S. application Ser. No. 12/703,118, incorporated herein in its entirety.

The connecting lines 1106, 1108 can, in some embodiments, include a distance indicator, such as a numerical display, or ruler tick marks. In some cases, the distance indicator can be superimposed on the connecting lines 1106, 1108, to show how far the intersection indicator 1110 is from the image region 304, and to show if it is moving toward or away from the image region 304. In some embodiments, the ruler's 0-mark can be anchored at the center of the intersection indicator 1110. In this way, even if the intersection indicator 1110 is off-screen, the user can see if it is moving closer to the image region 304 (which can be visible on-screen) because the ruler tick marks will appear to scroll toward the image region. Similarly, if the intersection-indicator is moving farther away from the image region 304, the tick marks can appear to scroll away from the image region 304.

In some embodiments the connecting line 1108 can connect to the center point (or some other point) of the intersection indicator 1110. However, when the medical device is almost parallel to the image plane (i.e. the angle between medical device and the image plane approaches zero degrees), the intersection indictor 1110 can fluctuate significantly. Accordingly, in certain embodiments, the connecting line 1108 can be constructed as follows: line 1106 can be determined from the center of the image region 304 to the point on the intersection indicator 1110 that is closest to the center of the image region 304. Where line 1106 intersects the edge of the image region 304, the connecting line 1108 can begin, and can continue until it reaches the intersection indicator 1110. In certain embodiments, the connecting line 1108 can be aligned such that it is perpendicular to the closest edge of the image region 304.

In some embodiments, the system can determine the emplacement of the medical device and the image region. In addition, the system can determine an axis and/or variance volume associated with the medical device does not intersect with the image plane within the image region and/or does not intersect with the image plane within the boundaries of the display screen. Based at least in part on this determination, the system can determine and display one or more visual indicators indicating that the axis/variance volume does not intersect with the image region 304, as described in greater detail above. In some cases in which the system 101 determines that the axis/variance volume intersects with the image plane outside the image region but within the display screen, the system 101 can display the intersection indicator 1110 outside the image region 304.

As described previously, the system can use an internal model for the length of the needle to determine whether the needle can reach a particular location inside the patient. For example, trajectory rings, similar to those described in greater detail in U.S. application Ser. No. 12/703,118, can extend forward of the tip, and be projected some distance forward of the tip, such as the needle length (distance from needle tip to needle handle), to allow the clinician to see when the needle is not long enough to reach the target. In certain embodiments, the system can display the intersection indicator in a different style (e.g. change the color, line width, symbol, line dashes, etc.) when distance from the intersection indicator to the medical device tip is greater than the length of the needle. This allows the user to know where the needle is aimed, but also determine that the needle cannot reach a particular location. Accordingly, in some embodiments, the system can determine a trajectory of the medical device and cause one or more displays to display trajectory indicators based at least in part on the length of the medical device.

Figure 12:
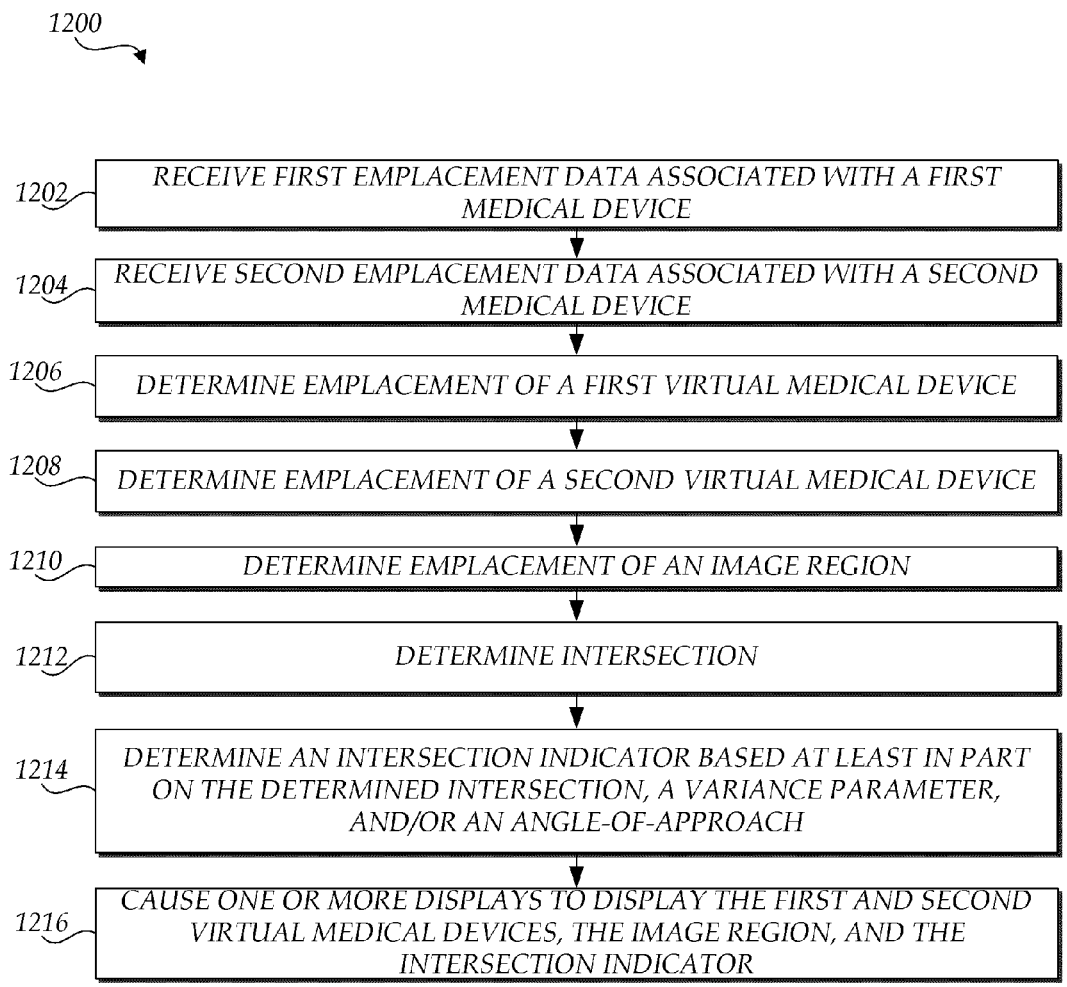
FIG. 12 is a flow diagram illustrative of an embodiment of a routine implemented by the system to display an intersection indicator.

FIG. 12 is a flow diagram illustrative of an embodiment of a routine 1200 implemented by the system 101 to display at least an intersection indicator. One skilled in the relevant art will appreciate that the elements outlined for routine 1200 can be implemented by one or more computing devices/components that are associated with the system 101, such as the position sensing unit 106, the image guidance unit 104, surgical system 108, and/or the imager 110. Accordingly, routine 1200 has been logically associated as being generally performed by the system 101. However, the following illustrative embodiment should not be construed as limiting. Furthermore, it will be understood that the various blocks described herein with reference to FIG. 12 can be implemented in a variety of orders. For example, the system may implement some blocks concurrently or change the order, as desired.

At block 1202, the system receives first emplacement data associated with a first medical device. At block 1204, the system receives second emplacement data associated with a second medical device. In certain embodiments, one of the medical devices can be a medical imaging device, as discussed in greater detail above. Furthermore, as mentioned above, the emplacement data associated with each medical device can be received from one or more device trackers associated with the respective medical device and/or from a position sensing unit that tracks the device trackers. In some embodiments, the emplacement data can include 3D coordinates and/or quaternion orientation coordinates.

At block 1206, the system determines an emplacement of a first virtual medical device corresponding to the first medical device based at least in part on the first emplacement data. In some embodiments, to determine the emplacement of the first virtual medical device, the system can map or transform the received emplacement data to a coordinate system associated with a virtual 3D space and/or the display screen. Furthermore, the system can use the characteristics (e.g., length, width, shape, location of tip, angle, location of the device tracker on the medical device, etc.) of the medical device to determine the emplacement of the virtual medical device. In some embodiments, the system can use a CAD file, 3D model, or other file to determine the characteristics of the medical device and to determine its emplacement.

In some embodiments, the virtual 3D space coordinate system and/or the display screen coordinate system can be based at least in part on a point-of-view location. Thus, the emplacement of the first virtual medical device (and other display objects) can be with respect to a point-of-view location). The point-of-view location can be a fixed location with respect to the display screen and/or can be a dynamic location. In some embodiments, when the point-of-view location is a fixed location it can correspond to a location that does not change during a medical procedure. For example, the fixed location can correspond to an expected location of a medical practitioner (e.g., presume that the medical practitioner will be 10 ft. in front of the display screen). In certain embodiments, the dynamic location can correspond to a location that can change during a medical procedure. For example, the system can track a medical practitioner during a medical procedure (e.g., by affixing a device tracker on the medical practitioner's head) and adjust the point-of-view location based at least in part on a real-time determination of the location of the medical practitioner.

At block 1208, the system determines an emplacement of a second virtual medical device corresponding to the second medical device based at least in part on the second emplacement data. The emplacement of the second virtual medical device can be determined in similar fashion to the emplacement of the first virtual medical device. For example, the system can map or transform the emplacement data to a coordinate system associated with the virtual 3D space and/or the display screen. In addition, the system can use the characteristics of the second medical device to determine its emplacement.

At block 1210, the system determines an emplacement of an image region based at least in part on the second emplacement data. In some embodiments, the system can use the characteristics of the second medical device to determine the location of the image region associated with the second medical device. For example, the characteristics may indicate a location of an imager on the medical device, as well as the specification of the image that is generated using the imager (e.g., height, width, and/or depth). Using this information, the system can determine the emplacement of the image region associated with the second medical device. Furthermore, the system can determine the emplacement of the image region directly from the second emplacement data and/or from the determined emplacement of the second virtual medical device. For example, the system can use a known relationship between the second emplacement data and the location of the image region (e.g., the image region begins 2 in. away from the of the second emplacement data location in a particular direction and ends 5 in. away) and/or use a known relationship between the emplacement of the second virtual medical device and the location of the image region (e.g., the image region begins 4 inches from the tip of the virtual medical device and ends at the tip of the virtual medical device).

At block 1212, the system determines an intersection. In certain cases, the intersection can correspond to an intersection of an axis associated with the first emplacement data and any display object (e.g., virtual medical device, image plane/region, other medical image data (e.g., CT scan, MM scan data), etc.). In some cases, the intersection can correspond to an intersection of an axis associated with the first emplacement data, or first emplacement data axis, and a plane associated with the second emplacement data, or second emplacement data plane. In some embodiments, the first emplacement data axis corresponds to an axis of the first medical device and/or the first virtual medical device and the second emplacement data plane corresponds to a plane associated with the second medical device and/or the second virtual medical device.

As mentioned above, using the first emplacement data, the system can determine a trajectory and/or axis associated with the first medical device (e.g., the first emplacement data axis). Similarly, the system can determine a plane associated with the second medical device using the second emplacement data (e.g., second emplacement data plane, image plane/region). In some embodiments, the determined plane can be parallel with a longitudinal axis of the second medical device and/or the second emplacement data plane. Using the first emplacement data axis and the second emplacement data plane, the system can determine an intersection. In some embodiments, the system can determine an intersection based at least in part on a determination that two objects are co-located as described in greater detail above.

At block 1214, the system determines an intersection indicator based at least in part on the determined intersection, a variance parameter associated with a device tracker that is associated with the first medical device, and/or an angle-of-approach. As mentioned above, in some embodiments, the first and/or second emplacement data can include some inaccuracy. Accordingly, the system can determine an intersection indicator taking into account the inaccuracy by using one or more variance parameters that are associated with the inaccuracy and/or the angle-of-approach.

In some embodiments, the system can determine the intersection indicator using an angle-of-approach, which can correspond to an angle difference between the first emplacement data axis and the second emplacement data plane (e.g., angle between the trajectory of the first medical device and the image plane/region). In certain embodiments, the size of the intersection indicator varies in proportion to the angle-of-approach. For example, as the angle-of-approach decreases, the size of the intersection indicator can increase.

In certain embodiments, the system can use an intersection of a variance volume associated with the first medical device (and/or the first emplacement data axis) with the image plane/region (and/or second emplacement data plane or axis) to determine the intersection indicator. For example, the intersection indicator can correspond to an area of intersection, the outline of the intersection on the image/plane/region, and/or the projection onto the image region of the intersections of the variance volume with portions of the image region. In some cases, the system can use an intersection of the variance volume associated with the first medical device with image width indicators (or any portions of the image region) to determine the intersection indicator. In some embodiments, the system can determine the intersection of the first emplacement data axis with the second emplacement data plane and generate an intersection indicator by determining an area or perimeter around the determined intersection. The area/perimeter can be determined using the variance parameter and/or the angle-of-approach.

At block 1216, the system causes one or more displays to concurrently display a perspective view of the first virtual medical device based at least in part on the determined emplacement of the first virtual medical device, a perspective view of the second virtual medical device based at least in part on the determined emplacement of the second virtual medical device, a perspective view of the image region based at least in part on the determined emplacement of the image region, and the intersection indicator. It will be understood that the system 101 can map any images received from the second medical device and/or image data corresponding to the determined emplacement of the second medical device to the image region and/or display the mapped data as part of the image region.

As mentioned above, the display screen coordinate system can correspond to a point-of-view location and the various display objects (virtual medical devices, image region, intersection indicator, and other guidance cues) and their emplacements can be determined with respect to the point-of-view location. Accordingly, the system can cause one or more displays to display the perspective view of the display objects.

It will be understood that fewer, more, or different blocks can be used as part of the routine 1200. For example, the routine 1200 can include blocks for determining and displaying intersection indicators on one or more display objects other than the image region and/or a shaded region, as described in greater detail below with reference to FIGS. 10A and 10B, blocks for determining and displaying an image on an differently shaped/sized image region as described in greater detail below with reference to FIGS. 10A and 10B, and/or blocks for determining and displaying visual indicators indicating that the intersection is off-image and/or off-screen, as described in greater detail below with reference to FIGS. 14A and 14B

Figure 13:
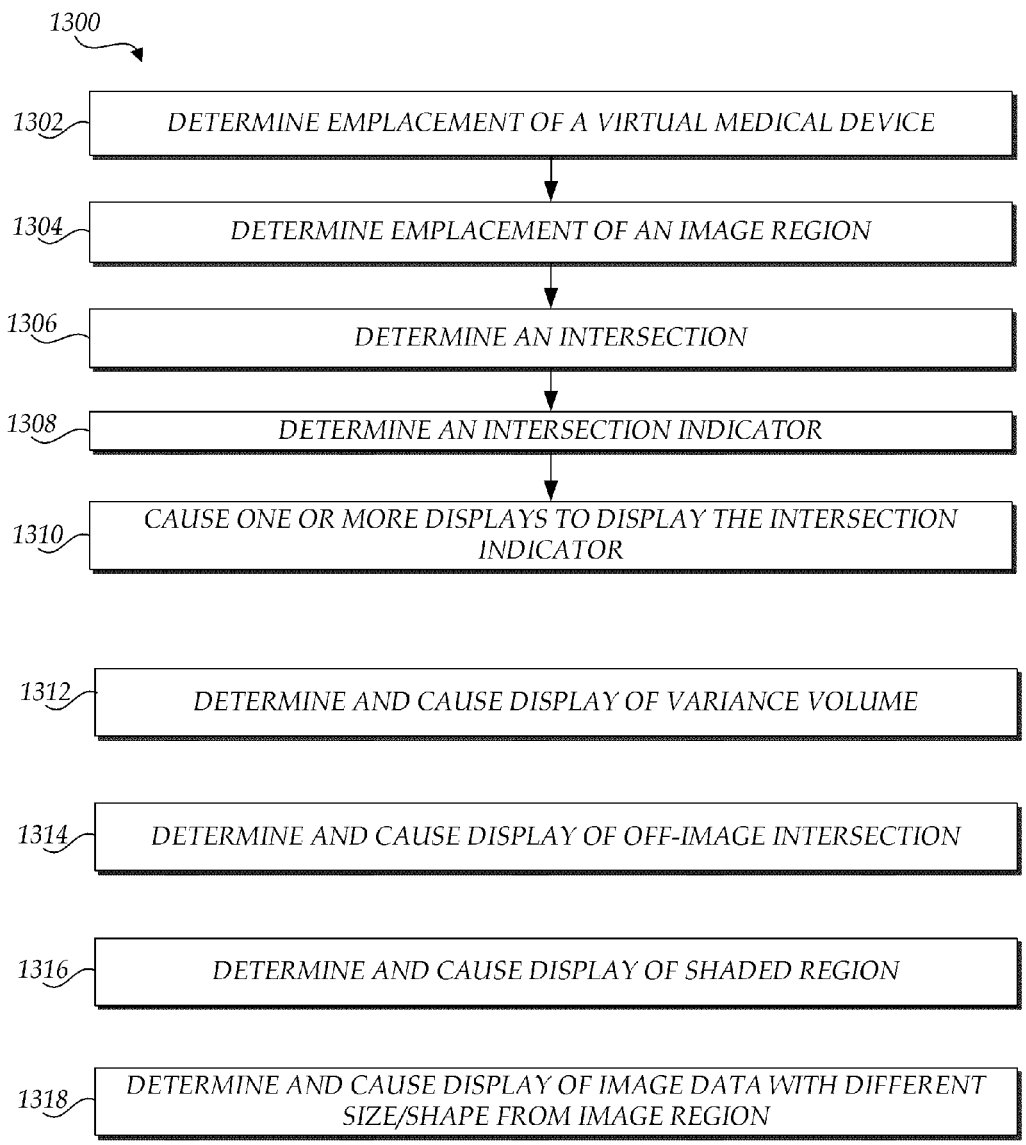
FIG. 13 is a flow diagram illustrative of an embodiment of a routine implemented by the system to display an intersection indicator.

FIG. 13 is a flow diagram illustrative of an embodiment of a routine 1300 implemented by the system 101 to display at least an intersection indicator. One skilled in the relevant art will appreciate that the elements outlined for routine 1300 can be implemented by one or more computing devices/components that are associated with the system 101, such as the position sensing unit 106, the image guidance unit 104, surgical system 108, and/or the imager 110. Accordingly, routine 1300 has been logically associated as being generally performed by the system 101. However, the following illustrative embodiment should not be construed as limiting. Furthermore, it will be understood that the various blocks described herein with reference to FIG. 13 can be implemented in a variety of orders. For example, the system may implement some blocks concurrently or change the order, as desired.

At block 1302, the system determines an emplacement of a first virtual medical device associated with a first medical device based at least in part on first emplacement data. As described above, the first emplacement data can correspond to a device tracker associated with a first medical device that corresponds to the first virtual medical device, and the first emplacement data can be received from the first device tracker and/or a position sensing unit.

At block 1304, the system determines an emplacement of an image region based at least in part on second emplacement data associated with a second medical device. As described above, the image region can be determined directly from the second emplacement data and/or using emplacement of a second medical device (or virtual medical device) that is associated with the image region.

At block 1306, the system determines an intersection based at least in part on the first emplacement data and the second emplacement data. As described om greater detail above, the intersection can correspond to an intersection between a first emplacement data axis and a second emplacement data plane, a variance volume/trajectory/axis and an image plane/region (or portions thereof), etc. In some embodiments, the intersection can correspond to an intersection between the first emplacement data axis, variance volume, trajectory, or axis with a display object, such as the virtual medical device, pre-operative data (e.g., blood vessel, organ, etc.), etc.

At block 1308, the system determines an intersection indicator based at least in part on the determined intersection. In some embodiments, the intersection indicator is further determined based at least in part on at least one of a variance parameter associated with a device tracker that is associated with the first medical device and/or an angle-of-approach. In certain embodiments, the size of the intersection varies in proportion to the angle-of-approach, as discussed in greater detail above.

At block 1310, the system causes one or more displays to display the intersection indicator. As described in greater detail above, the intersection indicator can be displayed in a perspective view in a virtual 3D space. The perspective view can be based at least in part on a point-of-view location.

It will be understood that fewer, more, or different blocks can be used as part of the routine 1300. For example, in some embodiments, the system 101 can cause the one or more displays to display one or more virtual medical devices, the image region, a medical image, one or more guidance cues, such as a trajectory indicator, etc. In certain embodiments, the routine 1300 can omit block 1308 and display an intersection indicator (block 1310) based on the determined intersection. In some embodiments the trajectory indicator can be based at least in part on the dimensions of the medical device. For example, the trajectory indicator can extend to a location that the medical device can reach based on its length. Furthermore, as non-limiting examples, the routine 1300 can include any one or any combination of blocks 1312, 1314, 1316, and/or 1318.

At block 1312, the system can determine and cause one or more displays to display a variance volume indicator based at least in part on a variance parameter associated with a device tracker that is associated with the first medical device.

At block 1314, the system can determine and cause one or more displays to display a visual indicator that the axis/variance volume does not intersect with the image region based at least in part on a determination that an axis and/or variance volume associated with the first virtual medical device intersects with a location outside the region but within a viewing area, and.

At block 1316, the system can determine and cause one or more displays to display a shaded region on the image region based at least in part on a determination that an axis and/or variance volume associated with the first virtual medical device intersects with a display object between the virtual medical device and an obstructed portion of the image region.

At block 1318, the system can determine and cause one or more displays to display portions of the image region outside a medical image differently than portions of the image region that overlap with the medical image based at least in part on a determination that the size and/or shape of the image region does not correspond to the size and/or shape of the medical image

TERMINOLOGY

Those having skill in the art will further appreciate that the various illustrative logical blocks, modules, circuits, and process steps described in connection with the implementations disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention. One skilled in the art will recognize that a portion, or a part, can comprise something less than, or equal to, a whole. For example, a portion of a collection of pixels can refer to a sub-collection of those pixels.

The various illustrative logical blocks, modules, and circuits described in connection with the implementations disclosed herein can be implemented or performed with a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be any conventional processor, controller, or microcontroller. A processor can also be implemented as a combination of computing devices, e.g., a combination of a DSP and a microprocessor, a plurality of microprocessors, one or more microprocessors in conjunction with a DSP core, or any other such configuration.

The steps of a method or process described in connection with the implementations disclosed herein can be embodied directly in hardware, in a software module executed by a processor, or in a combination of the two. A software module can include program instructions that instruct a hardware processor, and can be stored in RAM memory, flash memory, ROM memory, EPROM memory, EEPROM memory, registers, hard disk, a removable disk, a CD-ROM, or any other form of non-transitory computer-readable medium known in the art, as computer-executable instructions. An exemplary computer-readable storage medium is coupled to the processor such the processor can read information and/or computer-executable instructions from, and write information to, the computer-readable storage medium. In the alternative, the storage medium can be integral to the processor. The processor and the storage medium can reside in an ASIC or FPGA. The ASIC or FPGA can reside in a user terminal, camera, or other device. In the alternative, the processor and the storage medium can reside as discrete components in a user terminal, camera, or other device.

Headings are included herein for reference and to aid in locating various sections. These headings are not intended to limit the scope of the concepts described with respect thereto. Such concepts can have applicability throughout the entire specification.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Language such as the phrase "at least one of X, Y and Z," and "at least one of X, Y or Z," unless specifically stated otherwise, is understood with the context as used in general to convey that an item, term, etc. may be either X, Y or Z, or any combination thereof. Thus, such language is not generally intended to imply that certain embodiments require at least one of X, at least one of Y and at least one of Z to each be present or exclusively X or exclusively Y or exclusively Z.

Unless otherwise explicitly stated, articles such as 'a' or 'an' should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

The previous description of the disclosed implementations is provided to enable any person skilled in the art to make or use the present invention. Various modifications to these implementations will be readily apparent to those skilled in the art, and the generic principles defined herein can be applied to other implementations without departing from the spirit or scope of the invention. Furthermore, although described above with reference to medical devices and procedures, it will be understood that the embodiments described herein can be applied to other systems in which objects are tracked and virtual representations are displayed on a display and/or systems in which multiple objects are displayed on a display within a virtual space, such as within a virtual 3D space. Thus, the present invention is not intended to be limited to the implementations shown herein but is to be accorded the widest scope consistent with the principles and novel features disclosed herein.

The invention claimed is:

1. A method, comprising:
receiving first emplacement data associated with a first device tracker associated with a first medical device;
receiving second emplacement data associated with a second device tracker associated with a second medical device;
determining emplacement of a virtual 3D rendering of the first medical device with respect to a point-of-view location based at least in part on the first emplacement data;
determining emplacement of an image region with respect to the point-of-view location based at least in part on the second emplacement data;
determining an intersection of an axis associated with the virtual 3D rendering of the first medical device and at least a portion of the image region based at least in part on the determined emplacement of the virtual 3D rendering of the first medical device and the determined emplacement of the image region;
determining an intersection indicator based at least in part on the determined intersection, a variance parameter of the first device tracker, and an orientation angle of the virtual 3D rendering of the first medical device with respect to the image region; and
causing one or more displays to concurrently display:
a perspective view of at least a portion of the virtual 3D rendering of the first medical device in a virtual 3D space based at least in part on the determined emplacement of the virtual 3D rendering of the first medical device,
a perspective view of at least a portion of the image region based at least in part on the determined emplacement of the image region, and
the intersection indicator, wherein an area of the intersection indicator increases in proportion to a decrease in the orientation angle.

2. A method, comprising:
receiving first emplacement data associated with a first medical device;
receiving second emplacement data associated with a second medical device;
determining emplacement of a first virtual medical device with respect to a point-of-view location based at least in part on the first emplacement data;
determining emplacement of an image region with respect to a point-of-view location based at least in part on the second emplacement data;
determining an intersection based at least in part on the first emplacement data and the second emplacement data; and
causing one or more displays to concurrently display:
a perspective view of at least a portion of the virtual medical device in a virtual 3D space based at least in part on the determined position and orientation of the virtual medical device,
a perspective view of at least a portion of the image region, and
an intersection indicator based at least in part on the determined intersection and an orientation angle of the first virtual medical device with respect to the image region, wherein a size of the intersection indicator increases in proportion to an increased difference between the determined orientation angle and a threshold angle.

3. The method of claim 2, wherein said determining the intersection comprises determining an intersection between an axis associated with the first medical device and a plane associated with the second medical device.

4. The method of claim 2, wherein a part of the at least a portion of the image region is displayed differently from another part of the at least a portion of the image region based at least in part on a determination that the intersection is outside the image region.

5. The method of claim 2, wherein said causing the display to display further comprises causing the one or more displays to display an arrow indicating a direction of a virtual medical device and/or the intersection indicator based at least in part on a determination that the intersection is outside the image region.

6. The method of claim 2, wherein said determining the intersection comprises determining an intersection between an axis associated with the first medical device and at least a plurality of planes of the image region.

7. The method of claim 2, wherein said determining the intersection comprises determining an intersection between an axis associated with the first medical device and an axis associated with a second virtual medical device associated with the second medical device.

8. The method of claim 7, wherein at least a portion of the intersection indicator is displayed on the second virtual medical device.

9. The method of claim 2, wherein the intersection is a first intersection, the method further comprising determining a second intersection based at least in part on the first emplacement data and third emplacement data associated with a display object, wherein the intersection indicator is displayed based at least in part on the first intersection and the second intersection.

10. The method of claim 9, further comprising determining an obstructed portion of the intersection indicator based at least in part on the second intersection, wherein the obstructed portion of the intersection indicator is not displayed or is displayed differently from an unobstructed portion of the intersection indicator.

11. The method of claim 9, further comprising determining an obstructed portion of the image region based at least in part on the second intersection, wherein the obstructed portion of the image region is displayed differently from an unobstructed portion of the image region.

12. The method of claim 2, wherein at least a portion of the intersection indicator is parallel to a side of the image region.

13. The method of claim 2, wherein a first portion of the intersection indicator is parallel to a first side of the image region and a second portion of the intersection indicator is parallel to a second side of the image region.

14. The method of claim 2, wherein the intersection indicator comprises two parallel lines and rounded ends.

15. The method of claim 2, wherein a medical image is mapped to the image region, and wherein portions of the image region that do not include the medical image are displayed differently than portions of the image region that include the medical image.

16. The method of Claim 1, further comprising:
determining a variance volume based at least in part on the variance parameter of the first device tracker and the emplacement of the virtual 3D rendering of the first medical device,
wherein said determining the intersection is based at least in part on an intersection of the variance volume and the image region, and
wherein said causing the display to display the intersection indicator is based at least in part on the intersection of the variance volume and the image region.

17. A system, comprising
one or more processors communicatively coupled with one or more displays; and
a non-transitory computer-readable storage medium storing computer-executable instructions that when executed by the one or more processors cause the one or more processors to:
receive first emplacement data associated with a first medical device;
receive second emplacement data associated with a second medical device;
determine emplacement of a first virtual medical device with respect to a point-of-view location based at least in part on the first emplacement data;
determine emplacement of an image region with respect to a point-of-view location based at least in part on the second emplacement data;
determine an intersection based at least in part on the first emplacement data and the second emplacement data; and
cause one or more displays to concurrently display:
a perspective view of at least a portion of the virtual medical device in a virtual 3D space based at least in part on the determined position and orientation of the virtual medical device,
a perspective view of at least a portion of the image region, and
an intersection indicator based at least in part on the determined intersection and an orientation angle of the first virtual medical device with respect to the image, wherein a size of the intersection indicator increases in proportion to an increased difference between the determined orientation angle and a threshold angle.

18. The system of claim 17, wherein the intersection is a first intersection, and wherein the computer-executable instructions further cause the one or more processors to determine a second intersection based at least in part on the first emplacement data and third emplacement data associated with a display object, wherein the intersection indicator is displayed based at least in part on the first intersection and the second intersection.

19. The system of claim 18, wherein the computer-executable instructions further cause the one or more processors to determine an obstructed portion of the intersection indicator based at least in part on the second intersection, wherein the obstructed portion of the intersection indicator is not displayed or is displayed differently from an unobstructed portion of the intersection indicator.

20. The system of claim 18, wherein the computer-executable instructions further cause the one or more processors to determine an obstructed portion of the image region based at least in part on the second intersection, wherein the obstructed portion of the image region is displayed differently from an unobstructed portion of the image region.

* * * * *